US008148110B2

(12) United States Patent
Blau et al.

(10) Patent No.: US 8,148,110 B2
(45) Date of Patent: Apr. 3, 2012

(54) DETECTION OF MOLECULAR INTERACTIONS BY β-LACTAMASE REPORTER FRAGMENT COMPLEMENTATION

(75) Inventors: Helen M. Blau, Menlo Park, CA (US); Robert F. Balint, Palo Alto, CA (US); Thomas S. Wehrman, Redwood City, CA (US); Jeng-Horng Her, San Jose, CA (US)

(73) Assignees: The Board of Trustees of the Leland Stanford Junior University, Palo Alto, CA (US); KaloBios, Inc., South San Francisco, CA (US)

( * ) Notice: Subject to any disclaimer, the term of this patent is extended or adjusted under 35 U.S.C. 154(b) by 1106 days.

(21) Appl. No.: 10/330,811

(22) Filed: Dec. 26, 2002

(65) Prior Publication Data
US 2003/0175836 A1 Sep. 18, 2003

Related U.S. Application Data

(63) Continuation-in-part of application No. 09/526,106, filed on Mar. 15, 2000, now abandoned.

(60) Provisional application No. 60/344,757, filed on Dec. 26, 2001, provisional application No. 60/175,968, filed on Jan. 13, 2000, provisional application No. 60/135,926, filed on May 25, 1999, provisional application No. 60/124,339, filed on Mar. 15, 1999.

(51) Int. Cl.
*C12P 21/04* (2006.01)
(52) U.S. Cl. ............ 435/69.7; 435/6; 435/7.1; 435/7.32; 435/7.9; 435/69.8
(58) Field of Classification Search ................ 435/69.7, 435/69.8, 32, 479, 489, 465, 462, 463, 477
See application file for complete search history.

(56) References Cited

U.S. PATENT DOCUMENTS

| | | | | |
|---|---|---|---|---|
| 3,710,933 | A * | 1/1973 | Fulwyler et al. ............... 209/3.1 |
| 4,378,428 | A * | 3/1983 | Farina et al. ................. 435/7.23 |
| 4,708,929 | A | 11/1987 | Henderson |
| 4,978,613 | A * | 12/1990 | Bieniarz et al. ................. 435/18 |
| 5,223,393 | A | 6/1993 | Khanna et al. |
| 5,362,625 | A | 11/1994 | Krevolin et al. |
| 5,503,977 | A | 4/1996 | Johnsson et al. |
| 5,585,245 | A | 12/1996 | Johnsson et al. |
| 5,605,793 | A * | 2/1997 | Stemmer ........................... 435/6 |
| 5,741,657 | A * | 4/1998 | Tsien et al. ...................... 435/18 |
| 5,811,238 | A * | 9/1998 | Stemmer et al. .................. 435/6 |
| 5,830,721 | A * | 11/1998 | Stemmer et al. ............. 435/489 |
| 5,955,604 | A | 9/1999 | Tsien et al. |
| 6,117,679 | A * | 9/2000 | Stemmer ........................ 435/440 |
| 6,132,970 | A * | 10/2000 | Stemmer ............................ 435/6 |
| 6,165,793 | A * | 12/2000 | Stemmer ........................ 435/440 |
| 6,180,406 | B1 * | 1/2001 | Stemmer ........................ 435/440 |
| 6,270,964 | B1 * | 8/2001 | Michnick et al. .................. 435/6 |
| 6,277,638 | B1 * | 8/2001 | Stemmer ........................ 435/440 |
| 6,287,861 | B1 * | 9/2001 | Stemmer et al. .............. 435/440 |
| 6,291,242 | B1 * | 9/2001 | Stemmer ........................ 435/440 |
| 6,294,330 | B1 | 9/2001 | Michnick et al. |
| 6,297,053 | B1 * | 10/2001 | Stemmer ........................ 435/440 |
| 6,323,030 | B1 * | 11/2001 | Stemmer ........................ 435/440 |
| 6,342,345 | B1 | 1/2002 | Blau et al. |
| 6,344,356 | B1 * | 2/2002 | Stemmer ........................ 435/440 |
| 6,372,497 | B1 * | 4/2002 | Stemmer ........................ 435/440 |
| 6,395,547 | B1 * | 5/2002 | Stemmer ........................ 435/440 |
| 6,413,774 | B1 * | 7/2002 | Stemmer et al. .............. 435/440 |
| 6,444,468 | B1 * | 9/2002 | Stemmer et al. .............. 435/440 |
| 6,472,205 | B1 * | 10/2002 | Tsien et al. .................... 435/325 |
| 6,506,603 | B1 * | 1/2003 | Stemmer ............................ 435/6 |
| 6,518,065 | B1 * | 2/2003 | Stemmer ........................ 435/440 |
| 6,576,467 | B1 * | 6/2003 | Stemmer ........................ 435/440 |
| 6,828,099 | B2 * | 12/2004 | Michnick et al. .................. 435/6 |
| 6,872,871 | B2 * | 3/2005 | Brisson et al. ................. 800/288 |
| 7,062,219 | B2 | 6/2006 | Michnick et al. |
| 2002/0155502 | A1 * | 10/2002 | Balint et al. .................... 435/7.1 |

(Continued)

FOREIGN PATENT DOCUMENTS

CA 2196496 7/1998

(Continued)

OTHER PUBLICATIONS

Oliphant, A.R. & Struhl, K. An efficient method for generating proteins with altered enzymatic properties: Application to beta-lactamase. Proc. Natl. Acad. Sci. USA. 1989;86:9094-9098.*
Michnick, S.W. et al. Detection of protein-protein interactions by protein fragment complementation strategies. Methods Enzymol. 2000;328:208-230.*
Spencer, D.M., et al. Controlling signal transduction with synthetic ligands. Science. 1993;262:1019-1024.*
Amara, J.F. et al. A versatile synthetic dimerizer for the regulation of protein-protein interactions. Proc. Natl. Acad. Sci. USA. 1997;94:10618-10623.*
Rollins, C.T. et al. A ligand-reversible dimerization system for controlling protein-protein interactions. Proc. Natl. Acad. Sci. USA. 2000;97:7096-7101.*

(Continued)

*Primary Examiner* — Bao Thuy L Nguyen
*Assistant Examiner* — Gary W Counts
(74) *Attorney, Agent, or Firm* — David J. Aston; Peters Verny, LLP

(57) ABSTRACT

Methods and compositions for detecting molecular interactions, particularly protein-protein interactions, using at least two inactive, weakly-complementing β-lactamase fragments are provided. The invention allows detection of such interactions in eukaryotic and mammalian cells, in situ or in vitro. Detection of molecular interactions in mammalian cells is not limited to the nuclear compartment, but can be accomplished in the cytoplasm, cell surface, organelles, or between these entities. Methods provided utilize novel compositions comprising fusion proteins between molecules of interest and inactive, weakly-complementing β-lactamase fragments. Association of the molecules of interest brings the corresponding complementary β-lactamase fragments into close enough proximity for complementation to occur and β-lactamase activity to be observed. The invention is useful in the study of protein-protein interactions, functional genomics, agonist and antagonist screening and drug discovery.

37 Claims, 4 Drawing Sheets

U.S. PATENT DOCUMENTS

| | | | | |
|---|---|---|---|---|
| 2003/0165825 | A1* | 9/2003 | Balint et al. | 435/6 |
| 2004/0038317 | A1* | 2/2004 | Balint et al. | 435/7.2 |
| 2005/0079547 | A1* | 4/2005 | Michnick et al. | 435/7.1 |

FOREIGN PATENT DOCUMENTS

| | | |
|---|---|---|
| EP | 0 601 889 | 6/1994 |
| WO | WO 95/07463 | 3/1995 |
| WO | 95/29195 | 11/1995 |
| WO | WO 96/23810 | 8/1996 |
| WO | WO 96/30540 | 10/1996 |
| WO | WO 96/41166 | 12/1996 |
| WO | WO 98/34120 | 8/1998 |
| WO | WO 98/44350 | 10/1998 |
| WO | 99/28746 | 6/1999 |
| WO | 00/07038 | 2/2000 |
| WO | 00/71565 | 11/2000 |
| WO | WO 00/71702 | 11/2000 |
| WO | WO 01/51629 * | 7/2001 |
| WO | WO 03/058197 | 7/2003 |

OTHER PUBLICATIONS

Koide, K. et al. A synthetic library of cell-permeable molecules. J. Am. Chem. Soc. 2001;123:398-408.*

Adams, S. et al. (1991). "Fluorescence Ratio Imaging of Cyclic AMP in Single Cells," *Nature* 349:694-697.

Alberti, S. et al. (1987). "A Single Laser Method for Subtraction of Cell Autofluorescence in Flow Cytometry," *Cytometry* 8:114-119.

Bai, C. and Elledge, S. J. (1996). "Gene Identification Using the Yeast Two-Hybrid System," *Meth. Enzymol.* 273:331-347.

Beckwith, J.R. (1964). "A Deletion Analysis of the *Lac* Operator Region in *Escherichia coli,*" *J. Mol. Biol.* 8:427-430.

Beerli, R. R. and Hynes, N. E. (1996). "Epidermal Growth Factor-Related Peptides Activate Distinct Subsets of ErbB Receptors and Differ in Their Biological Activities" *J. Biol. Chem.* 271(11):6071-6076.

Belshaw, P. J. et al. (1996). "Controlling Protein Association and Subcellular Localization with a Synthetic Ligand that Induces Heterodimerization of Proteins," *Proc. Natl. Acad. Sci. USA* 93:4604-4607.

Benezra, R. et al. (1990). "The Protein Id: A Negative Regulator of Helix-Loop-Helix DNA Binding Proteins," *Cell* 61:49-59.

Blakely, B. T. et al. (2000). "Epidermal Growth Factor Receptor Dimerization Monitored in Live Cells," *Nature Biotechnol.* 18:218-222.

Blau, H. et al. (1983). "Cytoplasmic Activation of Human Nuclear Genes in Stable Heterocaryons," *Cell* 32:1171-1180.

Blau, H. (1992). "Differentiation Requires Continuous Active Control," *Annu. Rev. Biochem.* 61:1213-1230.

Bronstein, I. et al. (1989). "1,2-Dioxetanes: Novel Chemiluminescent Enzyme Substrates. Applications to Immunoassays" *J. Biolumin. Chemilumin.* 4:99-111.

Brown, E. J. et al. (1994). "A Mammalian Protein Targeted by G1-Arresting Rapamycin-Receptor Complex" *Nature* 369: 756-758.

Capecchi, M.R. (1989). "Altering the Genome by Homologous Recombination," *Science* 244(4910): 1288-1292.

Chaibi, E. B. et al (1999). "Inhibitor-Resistant TEM β-Lactamases: Phenotypic, Genetic and Biochemical Characteristics," *J. Antimicrob. Chemother.* 43:447-458.

Chen, J. et al., (1995) "Identification of an 11-kDa FKBP12-Rapamycin-Binding Domain within the 289-kDa FKBP12-Rapamycin-Associated Protein and Characterization of a Critical Serine Residue" (1995) *Proc. Natl. Acad. Sci. USA* 92:4947-4951.

Chen, C. M. et al., (1996) "I-mf, a Novel Myogenic Repressor, Interacts with Members of the MyoD Family" *Cell* 86:731-741.

Chen, Z-F., (1995) "*Twist* is Required in Head Mesenchyme for Cranial Neural Tube Morphogenesis," *Genes Devel.* 9:686-699.

Chervaux, C. et al. (1995). "Secretion of Active β-Lactamase to the Medium Mediated by the *Escherichia coli* Haemolysin Transport Pathway," *Mol. Gen. Genet.* 249:237-245.

Choi, J. et al. (1996) "Structure of the FKBP12-rapamycin Complex Interacting with the Binding Domain of Human FRAP," *Science* 273:239-242.

Cossu, G. et al., (1996) "How is Myogenesis Initiated in the Embryo?" *Trends Genet.* 12:218-223.

Dhawan, J. et al., (1991) "Systemic Delivery of Human Growth Hormone by Injection of Genetically Engineered Myoblasts" *Science* 254:1509-1512.

Felder, S. et al., (1992) "Kinetics of Binding, Endocytosis, and Recycling of EGF Receptor Mutants" *J. Cell. Biol.* 117:203-212.

Fields, S. et al. (1989) "A Novel Genetic System to Detect Protein-Protein Interactions"(1989) *Nature* 340:245-246.

Fiering, S. et al., (1991) "Improved FACS-Gal: Flow Cytometric Analysis and Sorting of Viable Eukaryotic Cells Expressing Reporter Gene Constructs" *Cytometry* 12:291-301.

Fiering, S. et al. (1995). "Targeted Deletion of 5'HS2 of the Murine B-Globin LCR Reveals That It Is not Essential for Proper Regulation of the β-Globin Locus," *Genes Dev.* 9:2203-2213.

Fuchtbauer, E. (1995). "Expression of M-Twist During Postimplantation Development of the Mouse," *Dev. Dyn* 204:316-322.

Gadella, T. et al. (1995). "Oligomerization of Epidermal Growth Factor Receptors on A431 Cells Studied by Time-Resolved Fluorescence Imaging Microscopy. A Stereochemical Model for Tyrosine Kinase Receptor Activation," *J. Cell Biol.* 129(6):1543-1558.

Hebrok, M. et al. (1994). "M-Twist is an Inhibitor of Muscle Differentiation," *Dev. Biol.* 165:537-544.

Hinrichs, W. et al. (1994). "Structure of the Tet Repressor-Tetracycline Complex and Regulation of Antibiotic Resistance," *Science* 264(5157):418-420.

Ho, S. N. et al. (1996). "Dimeric Ligands Define a Role for Transcriptional Activation Domains in Reinitiation," *Nature* 382:822-826.

Hu, J. et al. (1992). "HEB, a Helix-Loop-Helix Protein Related to E2A and ITF2 that can Modulate the DNA-Binding Ability of Myogenic Regulatory Factors," *Mol. Cell. Biol.* 12(3):1031-1042.

Hughes, S. M. and Blau, H. (1990). "Migration of Myoblasts Across Basal Lamina During Skeletal Muscle Development," *Nature* 345:350-353.

Jackson, D. A. et al., (1969) "Restoration of Enzymic Activity by Complementation in vitro Between Mutant α Subunits of Tryptophan Synthetase and Between Mutant Subunits and Fragments of the α Subunit" *J. Biol. Chem.* 244:4539-4546.

Jacobson, R. H. et al., (1994) "Three-Dimensional Structure of β-galactosidase from *E. coli*" *Nature* 369:761-766.

Jämsä, E. et al. (1995). "In Vivo Reactivation of Heat-Denatured Protein in the Endoplasmic Reticulum of Yeast," *EMBO J.* 14(23):6028-6033.

Johnsson, N. and Varshavsky, A. (1994). "Split Ubiquitin as a Sensor of Protein Interactions in Vivo," *Proc. Natl. Acad Sci. USA* 91:10340-10344.

Kinsella, T. and Nolan, G. (1996). "Episomal Vectors Rapidly and Stably Produce High-Titer Recombinant Retrovirus," *Hum. Gen. Ther.* 7:1405-1413.

Kitamura, T. et al. (1995). "Efficient Screening of Retroviral cDNA Expression Libraries," *Proc. Natl. Acad Sci. USA* 92:9146-9150.

Kiyokawa, N. et al., (1997) "Mitosis-specific Negative Regulation of Epidermal Growth Factor Receptor, Triggered by a Decrease in Ligand Binding and Dimerization, Can be Overcome by Overexpression of Receptor" *J. Biol. Chem.* 272(30):18656-18665.

Lassar, A. B. et al (1991). "Functional Activity of Myogenic HLH Proteins Requires Hetero-Oligomerization with E12/E47-Like Proteins in Vivo," *Cell* 66:305-315.

Levitzki, A. and Gazit, A. (1995). "Tyrosine Kinase Inhibition: an Approach to Drug Development," *Science* 267:1782-1788.

Livneh, E. et al., (1986) "Reconstitution of Human Epidermal Growth Factor Receptors and its Deletion Mutants in Cultured Hamster cells" *J. Biol. Chem.* 261:12490-12497.

Luo, Y. et al. (1997). "Mammalian Two-Hybrid System: A Complementary Approach to the Yeast Two-Hybrid System," *BioTechniques* 22(2):350-352.

Minden, J.S., "Synthesis of a New Substrate for Detection of *lacZ* Gene Expression in Live *Drosophila* Embryos" (1996) *BioTechniques* 20(1):122-129.

Miyawaki, A. et al. (1997). "Fluorescent Indicators for $Ca^{2+}$ Based on Green Fluorescent Proteins and Calmodulin," *Nature* 388:882-887.

Mohler, W. and Blau, H. (1996). "Gene Expression and Cell Fusion Analyzed by *lacz* Complementation in Mammalian Cells," *Proc. Natl. Acad. Sci. USA* 93:12423-12427.

Molkentin, J. D. et al., (1996) "Mutational Analysis of the DNA Binding, Dimerization, and Transcriptional Activation Domains of MEF2C" *Mol. Cell. Biol.* 16:2627-2636.

Moore, J. T. et al. (1997). "The Development of β-Lactamase as a Highly Versatile Genetic Reporter for Eukaryotic Cells," *Anal. Biochem* 247:203-209.

Murre, C. et al. (1989). "A New DNA Binding and Dimerization Motif in Immunoglobulin Enhancer Binding, Daughterless, *Myod*, and *Myc* Proteins," *Cell* 56:777-783.

Muthuswamy, S. K. et al. (1999). "Controlled Dimerization of ErbB Receptors Provides Evidence for Differential Signaling by Homo- and Heterodimers," *Mo.l Cell. Biol.* 19(10):6845-6857.

Nolan, G. P. et al., (1988) "Fluorescence-Activated Cell Analysis and Sorting of Viable Mammalian Cells Based on β-D-Galactosidase Activity After Transduction of *Escherichia coli lacZ*" *Proc. Natl. Acad. Sci. USA* 85:2603-2607.

Olson, E. N. et al. (1996). "Know Your Neighbors: Three Phenotypes in Null Mutants of the Myogenic bHLH Gene MRF4," *Cell* 85:1-4.

Ott, M.-O. et al. (1991). "Early Expression of the Myogenic Regulatory Gene, *myf-5*, in Precursor Cells of Skeletal Muscle in the Mouse Embryo," *Development* 111:1097-1107.

Otto, K. G. et al. (2001). "Cell Proliferation Through Forced Engagement of C-Kit and Flt-3;" *Blood* 97(11):3662-3664.

Parks, D. R. et al., (1986) "Chapter 29: Flow cytometry and fluorescence activated cell sorting (FACS)" *The Handbook of Experimental Immunology*, (eds. Weir, D.M., Herzenberg, L.A., Blackwell, C.C. & Herzenberg, L.A.), Blackwell, Edinburgh, 4th edition, pp. 29.1-29.21.

Pear, W. S. et al (1993). "Production of High-Titer Helper-Free Retroviruses by Transient Transfection," *Proc. Natl. Acad. Sci USA* 90:8392-8396.

Philippon, A. et al. (1998). "The Diversity, Structure and Regulation of β-Lactamases," *Cell Mol. Life Sci* 54:341-346.

Pookanjanatavip, M. et al. (1992) Subunit Complementation of Thymidylate Synthase *Biochemistry* 31:10303-10309.

Prentki, P., (1992) "Nucleotide Sequence of the Classical *lacZ* deletion ΔM15" *Gene* 122:231-232.

Rastinejad, F. and Blau, H. M. (1993) "Genetic Complementation Reveals a Novel Regulatory Role for 3' Untranslated Regions in Growth and Differentiation," *Cell* 72:903-917.

Remy, I. and Michnick, S. (1999). "Clonal Selection and in Vivo Quantitation of Protein Interactions with Protein-Fragment Complementation Assays," *Proc. Natl. Acad. Sci. USA* 96:5394-5399.

Remy, I. et al. (1999). "Erythropoietin Receptor Activation by a Ligand-Induced Conformation Change," *Science* 283:990-993.

Riviere, I. et al. (1995). "Effects of Retroviral Vector Design on Expression of Human Adenosine Deaminase in Murine Bone Marrow Transplant Recipients Engrafted with Genetically Modified Cells," *Proc. Natl. Acad. Sci USA* 92:6733-6737.

Rohwedel, J. et al. (1995). "*M-Twist* Expression Inhibits Mouse Embryonic Stem Cell-Derived Myogenic Differentiation in Vitro," *Exp. Cell. Res.* 220:92-100.

Rossi, F. et al. (1997). "Monitoring Protein-Protein Interactions in Intact Eukaryotic Cells by β-Galactosidase Complementation," *Proc. Natl Acad. Sci USA* 94:8405-8410.

Rossi, F. et al. (2000). "Interaction Blues: Protein Interactions Monitored in Live Mammalian Cells by B-Galactosidase Complementation," *Trends Cell Biol.* 10:119-122.

Rotman, B. et al. (1963) "Fluorogenic Substrates for β-D-Galactosidases and Phosphatases Derived from Fluorescein (3,6-dihydroxyfluoran) and its Monomethyl Ether" *Proc. Natl. Acad. Sci. USA* 50:1-6.

Rudnicki, M. A. et al. (1992). "Inactivation of *MyoD* in Mice Leads to Up-Regulation of the Myogenic HLH Gene Myf-5 and Results in Apparently Normal Muscle Development," *Cell* 71:383-390.

Schlessinger, J. et al (1992). "Growth Factor Signaling by Receptor Tyrosine Kinases," *Neuron* 9:383-391.

Simonen, M et al. (1994). "The Role of the Carrier Protein and Disulfide Formation in the Folding of β-Lactamase Fusion Proteins in the Endoplasmic Reticulum of Yeast," *J. Biol. Chem.* 269(19):13887-13892.

Smith, T. H. et al. (1994). "Somite Subdomains, Muscle Cell Origins, and the Four Muscle Regulatory Factor Proteins," *J. Cell. Biol.* 127(1):95-105.

Spicer, D. B. et al. (1996). "Inhibition of Myogenic bHLH and MEF2 Transcription Factors by the bHLH Protein Twist," *Science* 272:1476-1480.

Stoetzel, C. et al. (1995). "Dorso-Ventral and Rostro-Caudal Sequential Expression of *M-Twist* in the Postimplantation Murine Embryo," *Mech. Dev.* 51:251-263.

Tajbakhash, S. et al. (1996). "Muscle Progenitor Cells Failing to Respond to Positional Cues Adopt Non-Myogenic Fates in Myf-5 Null Mice," *Nature* 384:266-270.

Tajbakhsh, S. and Buckingham, M. E. (1994). "Mouse Limb Muscle is Determined in the Absence of the Earliest Myogenic Factor Myf-5," *Proc. Natl. Acad. Sci USA* 91:747-751.

Tajbakhsh, S. et al. (1996). "A Population of Myogenic Cells Derived From the Mouse Neural Tube," *Neuron* 13:813-821.

Thomas, K. and Capecchi, M. (1986). "Introduction of Homologous DNA Sequences into Mammalian Cells Induces Mutations in the Cognate Gene," *Nature* 324:34-38.

Ullman, A. et al., (1967) "Characterization by in vitro Complementation of a Peptide Corresponding to an Operator-Proximal Segment of the β-galactosidase Structural Gene of *Escherichia coli*" *J. Mol. Biol.* 24:339-343.

Ullman, A. et al. (1968). "On the Subunit Structure of Wild-Type Versus Complemented β-Galactosidase of *Escherichia coli,*" *J. Mol. Biol.* 32:1-13.

Ullman, A. et al. (1965). "Identification Par Complémentation in Vitro Et Purification D'un Segment Peptidique De La B-Galactosidase D'*Escherichia coli,*" *J. Mol. Biol.* 12:918-923 (Original Version).

Ullrich, A. and Schlessinger, J. (1990). "Signal Transduction by Receptors with Tyrosine Kinase Activity," *Cell* 61:203-212.

Ward, V. K. et al. (1995). "Generation of an Expression Library in the Baculovirus Expression Vector System," *Journal of Virological Methods* 53:263-272.

Webster, C. et al. (1988) "Isolation of Human Myoblasts With the Fluorescence-Activated Cell Sorter" (1988) *Exp. Cell Research* 174:252-265.

Weiss, F. U. et al. (1997). "Novel Mechanisms of RTK Signal Generation," *Curr. Opinion Genet. Dev.* 7:80-86.

Yan, K. et al. (1996). "Differential Ability to Form the G Protein βγ Complex Among Members of the β and γ Subunit Families," *Journal of Biological Chemistry* 271(12):7141-7146.

Yarden, Y. et al. (1987). "Epidermal Growth Factor Induces Rapid, Reversible Aggregation of the Purified Epidermal Growth Factor Receptor," *Biochemistry* 26:1443-1451.

Yun, K. and Wold, B. (1996). "Skeletal Muscle Determination and Differentiation: Story of a Core Regulatory Network and its Context," *Curr. Opin Cell. Biol* 8:877-889.

Zlokarnik, G. et al. (1998). "Quantitation of Transcription and Clonal Selection of Single Living Cells with β-Lactamase as Reporter," *Science* 279:84-88.

Arndt et al., "A Heterodimeric Coiled-coil Peptide Pair Selected in Vivo from a Designed Library-versus-Library Ensemble", J. Mol. Biol, 2000, 295:627-639.

Bartel et al., "A protein linkage map of *Escherichia coli* bacteriphage T7", Nature Genetic, Jan. 12, 1996, 12:72.

Bartel et al., "Short Technical Reports; Elimination of false positives that arise in using the two-hybrid system", Biotechniques, 1993, 14(6):920.

Betton et al., "Creating a bifunctional protein by insertion of beta-lactamase into the maltodextrin-binding protein", Nature Biotechnology, 1997, 15:1276-9.

Cubitt et al., "Understanding, Improving and using green fluorescent proteins", Trends Biochem, Nov. 1995, 20:448.

Defeo-Jones, et al., "Cloning of cDNAs for cellular proteins that bind to the retinoblastoma gene product", Nature, Jul. 18, 1991, 352:251.

Fremont-Racine et al., "Toward a functional analysis of the yeast genome through exhaustive two-hybrid screens", Nature Genetics, Jul. 1997, 16:277.

Galarneau et al., "Beta-Lactamase protein fragment complementation assays as in vivo and in vitro sensors of protein-protein interactions", Nature Biotechnology, 2002, 20:619-22.

Krebber et al., "Selectively-infective Phase (SIP): A mechanistic dissection of a novel in vivo selection for protein-ligand interactions", J Mol Biol, 1997, 268:607-18.

Krebber et al., Reliable cloning of functional antibody variable domains from hybridomas and spleen cell repertoires employing a reengineered phage display system, J. Immunol Methods, 1997, 201:35-55.

Lu, Zhijian; et al., "Expression of Thioredoxin Random Peptide Libraries on the *Escherichia coli* Cell Surface as Functional Fusions to Flagellin: A System Designed for Exploring Protein-Protein Interactions", 1995, Biotechnology, 12:366-72.

Luban et al., "Human Immunodeficiency Virus Type 1 Gag Protein Binds to Cyclophilins A and B", Cell, 1993, 73:1067-78.

Mayeyraud, L.; et al., "Crystal Structure of an Acylation Transition-State Analog of the TEM-1 beta-Lactamase. Mechanistic Implications for Class A beta-Lactamases", Biochemistry, 1998, 37:2622-8.

Ostermeier et al., "Finding Cinderella's slipper—proteins that fit", Nature Biotechnology, Jul. 1999, 17:639-40.

Ostermeier et al., "A combinatorial approach to hybrid enzymes independent of DNA homology", Nature Biotechnology, Dec. 1999, 17(12):1205-9.

Pelletier et al., "A protein complementation assay for detection of protein-protein interactions in vivo", Protein Engineering, 1997, 10:89.

Pelletier et al., "An in vivo library-versus-library selection of optimized protein-protein interactions", Nature Biotechnology, 1999, 17:683-9.

Pieper et al., "Circularly permuted beta-lactamase from *Staphylococcus aureus* PC1", Biochemistry, 1997, 36 (29):8767-74.

Subramaniam et al., "Direct visualization of protein interactions in plant cells", Nature Biotechnology, 2001: 19:769-72.

Voet, D. and Voet, J. G., Biochemistry, Second Edition, New York: John Wiley and Sons, 1995, pp. 123-128 (Sections 6-3A) and p. 230, col. 2, first paragraph.

Vojtek et al., "Mammalian Ras Interacts Directly with the Serine/Threonine Kinase Raf", Cell, 1993, 74:205-14.

Zervos et al., "Mxi 1, a Protein that Specifically Interacts with Max to Bind Mayc-Max Recognition Sites", Cell, 1993, 72:223-32.

* cited by examiner

DETECTION OF MOLECULAR INTERACTIONS BY β-LACTAMASE REPORTER FRAGMENT COMPLEMENTATION

CROSS-REFERENCE TO RELATED APPLICATIONS

This invention claims priority to U.S. Provisional Patent Application Ser. No. 60/344,757 filed Dec. 26, 2001, the disclosure of which is incorporated herein by reference in its entirety, and is a continuation-in-part of U.S. patent application Ser. No. 09/526,106, filed on Mar. 15, 2000, now abandoned which claims priority to U.S. Provisional Patent Application 60/175,968, filed on Jan. 13, 2000, U.S. Provisional Patent Application 60/135,926, filed on May 25, 1999, and U.S. Provisional Patent Application 60/124,339, filed on Mar. 15, 1999.

FEDERALLY-SPONSORED RESEARCH OR DEVELOPMENT

This invention was made with Government support under contract HD018179, awarded by the National Institutes of Health. The Government has certain rights in this invention.

TECHNICAL FIELD OF THE INVENTION

This invention relates generally to the field of molecular biology. More specifically, the invention provides methods and compositions for β-lactamase-derived reporter systems for detecting molecular interactions, particularly, but not limited to protein-protein interactions in mammalian cells.

BACKGROUND OF THE INVENTION

Homeostasis, proliferation, and differentiation in mammalian cells are regulated by the complex circuitry of interacting proteins. Perturbation of these interactions can lead to disease states such as cancer. Thus, analyzing protein-protein interactions is of extreme importance to understanding metazoan physiology.

Protein-protein interactions are involved in every cellular process ranging from gene expression and signal transduction to cell division and differentiation, yet they have been among some of the most difficult aspects of cell biology. Standard biochemical methods have yielded most of the available information about such interactions, but these assays are often limited by the available reagents such as monoclonal antibodies for immunoprecipitation, or lack of appropriate cellular context.

The development of fusion-protein based assays, such as the yeast two-hybrid method (Fields, S. & Song, O. (1989) *Nature* 340, 245-6.), have greatly expanded the potential for studying protein interactions in intact cells. However, this assay relies on the transcription of a reporter gene; consequently it is not applicable to studies of the kinetics of protein-protein interactions and is unable to detect the interaction of compartmentalized proteins such as receptors at the cell surface. A method based on fluorescence resonance energy transfer (FRET) provided a further advance and is currently one of the most accurate methods used to monitor dynamic interactions (Adams, S. R., Harootunian, A. T., Buechler, Y. J., Taylor, S. S. & Tsien, R. Y. (1991) *Nature* 349, 694-7.). However, the incremental changes in fluorescence assayed by FRET are small and the stringent steric requirements for detecting the interacting proteins can restrict the utility of this technique.

Assays based on the complementation of enzyme fragments fused to interacting proteins that regenerate enzymatic activity upon dimerization are particularly well suited to monitoring inducible protein interactions (reviewed in Rossi, F. M., Blakely, B. T. & Blau, H. M. (2000) *Trends Cell Biol.* 10, 119-122). These systems have important advantages including low level expression of the test proteins, generation of signal as a direct result of the interaction, and enzymatic amplification. As a result, they are highly sensitive and physiologically relevant assays (Blakely, B. T., Rossi, F. M., Tillotson, B., Palmer, M., Estelles, A. & Blau, H. M. (2000) *Nature Biotechnol.* 18, 218-22). Additionally, assays based on enzyme complementation can be performed in any cell type of interest or in diverse cellular compartments such as the nucleus, secretory vesicles or plasma membrane.

Systems for the study of protein-protein interactions have been described which utilize two fusion genes whose products reconstitute the function of a transcriptional activator. Fields et al., (1989) *Nature* 340:245-247; Bai et al., (1996) *Meth. Enzymol.* 273:331-347; Luo et al., (1997) *BioTechniques* 22(2):350-352. In one fusion gene, a sequence encoding a first protein is conjugated to a sequence encoding a DNA-binding domain of a transcriptional regulatory protein. In a second fusion gene, a sequence encoding a second protein is conjugated to a sequence encoding a transcriptional activation domain of a transcriptional regulatory protein. The two fusion genes are co-transfected into a cell which also contains a reporter gene whose expression is controlled by a DNA regulatory sequence that is bound by the DNA-binding domain encoded by the first fusion gene. Expression of the reporter gene requires that a transcriptional activation domain be brought adjacent to the DNA regulatory sequence. Binding of the first protein to the second protein will bring the transcriptional activation domain encoded by the second fusion gene into proximity with the DNA-binding domain encoded by the first fusion gene, thereby stimulating transcription of the reporter gene. Thus, the level of expression of the reporter gene will reflect the degree of binding between the first and second proteins.

There are several disadvantages associated with the use of the above-mentioned system. As it is dependent upon transcriptionally-regulated expression of a reporter gene, this system is limited to the assay of interactions that take place in the nucleus. In addition, the assay is indirect, relying on transcriptional activation of a reporter gene whose product is diffusible. Hence, a method which would allow a direct and immediate examination of molecular interactions, at the site where they occur, would be desirable.

A system for detecting protein-protein interactions, not limited to nuclear interactions, has been described in U.S. Pat. Nos. 5,503,977 and 5,585,245. In this system, fusions between potential interacting polypeptides and mutant subunits of the protein Ubiquitin are formed. Juxtaposition of the two Ubiquitin subunits brought about by interaction between potential interacting polypeptides which creates a substrate for a Ubiquitin-specific protease, and a small peptide reporter fragment is released. In this system, binding between the potential interacting polypeptides does not generate any type of enzymatic activity. Therefore, signal amplification is not possible. Additionally, the ubiquitin system does not measure in situ activity in intact cells, but relies on assays of proteolysis in cell-free extracts. What is needed is a sensitive method for examining protein interactions in intact cells in the relevant cellular compartment.

The possibility of enzyme fragment complementation with beta-galactosidase (β-gal) was first shown in prokaryotes. (Ullman, A. et al. *J. Mol. Biol.* 24, 339-343 (1967); Ullman, A. et al. *J. Mol. Biol* 32, 1-13 (1968); Ullman, A. et al. *J. Mol. Biol.* 12, 918-923 (1965)). Later studies furthered this technology by extending β-gal complementation to mammalian cells and showing that it could be used to monitor inducible protein-protein interactions such as high affinity rapamycin binding proteins and epidermal growth factor (EGF) receptor dimerization. (Mohler, W. & Blau, H. (1996) *Proc. Natl. Acad. Sci. USA* 93, 12423-12427; Rossi, F., Charlton, C. & Blau, H. (1997) *Proc. Natl. Acad. Sci. USA* 94, 8405-8410; Blakely, B. et al. (2000) *Nat Biotechnol* 18, 218-222). U.S. Pat. No. 6,342,345 (Blau, et al.) discloses a enzyme fragment complementation system using beta-galactosidase (β-gal). An alternative complementation system utilized dihydrofolate reductase (DHFR) fragments to study erythropoietin receptor dimerization. (Remy, I. et al. (1999) *Science* 283, 990-993; Remy, I. & Michnick, S. (1999) *Proc. Natl. Acad. Sci. USA* 96, 5394-5399).

However, both DHFR and β-gal fragment complementation have their limitations. DHFR fragment complementation is measured by growth, where approximately 25 reconstituted DHFR molecules are required for cell survival. Remy, I. et al. (1999) *Science* 283, 990-993. Thus, the assay does not directly monitor real-time protein-protein interactions. Moreover, the DHFR interaction is stoichiometric and does not benefit from enzymatic amplification of the signal. Consequently, the signal is weak or requires significant overexpression of the fusion proteins. In addition, mammalian cells have endogenous DHFR, which may increase the background levels of enzyme activity.

The β-gal complementation system of U.S. Pat. No. 6,342,345 (Blau, et al.) and as described in the literature enzymatically amplifies of the signal and can be used to monitor interactions in live cells in real-time. (Rossi, F., Charlton, C. & Blau, H. (1997) *Proc. Natl. Acad. Sci. USA* 94, 8405-8410; Blakely, B. et al. (2000) *Nat Biotechnol* 18, 218-222). However, β-gal is a large 90 kD molecule which may sterically hinder the same interaction it seeks to monitor. In addition to the large size of the subunits, β-gal also has the disadvantage of being a tetrameric complex. The need to form a multimeric complex detracts from the usefulness of this system. β-gal also lacks a cell permeable substrate. Hypotonic shock, used to introduce the β-gal substrate into cells, is not ideal because it can affect substrate localization within the cell and can limit the amount of available substrate due to osmotic constraints.

What is desired is a complementation system that utilizes a small protein which has enzymatic activity to allow for signal amplification and a cell permeable substrate.

SUMMARY OF THE INVENTION

Class A β-lactamases are particularly attractive candidates for an assay based on enzyme fragment complementation due to the fact that they are monomeric and of relatively small size (Philippon, A., Dusart, J., Joris, B. & Frere, J. M. (1998) *Cell Mol Life Sci* 54, 341-6). In addition, β-lactamases have been successfully expressed in prokaryotic and eukaryotic cells, making this system applicable to both classes of organisms (Moore, J. T., Davis, S. T. & Dev, I. K. (1997) *Anal Biochem* 247, 203-9). An embodiment of the invention relates to the use in mammalian cells of a pair of β-lactamase fragments (α197 and ω198) that are known to complement well in bacteria when fused to two helices that form a leucine zipper. Detectable interactions according to this invention are not limited to these particular moieties, as interactions between larger proteins are also detectable.

Extension of the β-lactamase system into mammalian cells provides significant advantages over other fragment complementation systems currently employed (e.g. β-gal (Rossi, F., Charlton, C. A. & Blau, H. M. (1997) *Proc Natl Acad Sci USA* 94, 8405-10; DHFR (Remy, I. & Michnick, S. W. (1999) *Proc Natl Acad Sci USA* 96, 5394-9), because the fragments are small (<19 kDa), there is no endogenous β-lactamase activity, and a highly sensitive cell-permeable fluorescent substrate has recently been developed (Zlokainik, G., Negulescu, P. A., Knapp, T. E., Mere, L., Burres, N., Feng, L., Whitney, M., Roemer, K. & Tsien, R. Y. (1998) *Science* 279, 84-8). The β-lactamase fragments could be used to monitor inducible interactions in a mammalian cell line measured either by fluorescence microscopy or flow cytometry. The β-lactamase fragments could also detect inducible interactions in eukaryotic cells. Further, the observed β-lactamase complementation was a direct measure of enzyme activity, not dependent on de novo protein synthesis, and generated detectable signal within minutes of protein dimerization, making it applicable to the detection of transient protein interactions. This system has broad utility in monitoring protein interactions in diverse intracellular compartments in a range of cell types.

The present invention provides a novel approach for detecting molecular interactions in mammalian cells, particularly protein-protein interactions. In one embodiment, this invention provides a reporter system based on a first low affinity β-lactamase reporter fragment coupled to a first putative binding moiety; and a second low affinity β-lactamase reporter fragment coupled to a second putative binding moiety; wherein the first low affinity β-lactamase reporter fragment is capable of association with the second low affinity β-lactamase reporter fragment to generate a β-lactamase activity, said association being mediated by the binding of the first and second putative binding moieties. Preferably, the reporter system is used to detect protein-protein interactions in eukaryotic cells. More preferably, the reporter system is used to detect protein-protein interactions in mammalian cells.

In another embodiment, the invention provides a method of determining the occurrence of binding between first and second putative binding moieties in eukaryotic cells, the method comprising: a) providing a reporter system comprising a first component comprising a first low-affinity β-lactamase reporter fragment, coupled to the first putative binding moiety; and a second component comprising a second low-affinity β-lactamase reporter fragment coupled to the second putative binding moiety wherein the first low-affinity β-lactamase reporter fragment is capable of association with at least the second low-affinity β-lactamase reporter fragment to generate β-lactamase activity, said association being mediated by the binding of the first and second putative binding moieties; b) combining the first component and the second component; and c) detecting the presence or absence of the β-lactamase activity.

In a further embodiment, the invention provides a method of screening for binding of a first binding moiety with members of a plurality of different second putative binding moieties in mammalian cells, the method comprising: a) providing a plurality of reporter systems each comprising: a first component comprising a first low-affinity β-lactamase reporter fragment coupled to the first binding moiety, and one of a plurality of second components each comprising a second low-affinity β-lactamase reporter fragment coupled to one of said plurality of second putative binding moieties, wherein in each of said second components, said second putative binding moiety is different wherein the first low-affinity β-lactamase reporter fragment is capable of association with the second low-affinity β-lactamase reporter fragment to generate a β-lactamase activity upon the binding of the first binding moiety with one of said different second putative binding moieties; b) individually combining the first component with each of the plurality of second components in eukaryotic cells to produce a plurality of binding assay samples, each of which includes the first component and a different one of the second components; and c) detecting the presence or absence of the β-lactamase activity in each of the binding assay samples.

The invention additionally provides nucleic acids encoding fusion proteins including a low-affinity β-lactamase reporter fragment and a putative binding moiety, and the fusion proteins encoded by said nucleic acids. The invention further provides viral vectors comprising nucleic acids encoding such fusions proteins. The invention also provides eukaryotic cells, preferablt mammalian cells, transformed by the nucleic acids and viral vectors described above.

BRIEF DESCRIPTION OF THE FIGURES

FIG. 2A is a schematic of the bicistronic, retrovirally expressed fusion proteins FKBP12ω198 and α197FRB. FIG. 2B shows an immunofluorescence assay of β-lactamase activity. FIG. 2C shows a FACS analysis of β-lactamase activity.

FIG. 3A shows a time course of rapamycin induced dimerization. FIG. 3B shows a mean fluorescence time course. FIG. 3C shows the effect of inhibition of protein synthesis on rapamycin induced complementation.

FIG. 4A shows the membrane-bound and cytoplasmic fusion proteins which were co-expressed in C2C12 cells. FIG. 4B shows flow cytometry analysis of cells expressing fusion constructs.

DETAILED DESCRIPTION OF PREFERRED EMBODIMENTS

The present invention provides a broadly applicable protein-protein interaction biosensor, which has significant advantages over traditional biochemical as well as existing protein fragment complementation systems. This system should enable the identification of molecules that promote or inhibit key protein interactions via high-throughput screens in a range of cell types, phyla and species. Further, given its unique properties, β-lactamase may be particularly well suited to identifying novel protein interactions specific to subcellular compartments of transformed, proliferating and differentiating cell types via an eukaryotic two hybrid assay.

The present invention provides methods and compositions for detecting, assaying and quantitating molecular interactions within mammalian cells and in vitro, through complementation between two or more low affinity reporter fragments, such as distinct β-lactamase fragments. In a preferred embodiment, protein-protein interactions within the mammalian cells are detected and quantitated using the methods and compositions of the present invention. The practice of the present invention enables the study of protein-protein interactions and their control in living mammalian cells without reliance upon the transcriptional activation of a reporter gene construct. Association of the proteins of interest results directly in enzyme activity and is independent of other cellular functions. Therefore, the present invention provides advantages over other systems currently in use by allowing the detection of complexes that are excluded from the nucleus, and detection of complexes whose formation would inhibit transcription. Furthermore, the present invention allows the detection and localization of specific binding interactions within eukaryotic cells at different stages of development and differentiation, and an analysis of the induction or inhibition of binding interactions in mammalian cells.

Interactions occurring within the nucleus of the mammalian cell, interactions occurring in the cytoplasm, on the cell surface, within or on the surface of organelles, or between cytoplasmic and surface (either cellular or organellar) molecules, as well a interactions occurring outside the mammalian cell, are all capable of being detected in the practice of the present invention. Thus, the invention surmounts the limitations associated with previous assays for protein-protein interactions, which were either limited to interactions occurring in the nucleus, or did not always allow accurate localization of molecular interactions, and which were not well-suited for detection of interactions which resulted in inhibition of transcription or translation.

Protein Fragment Complementation Assays

Figure 1:
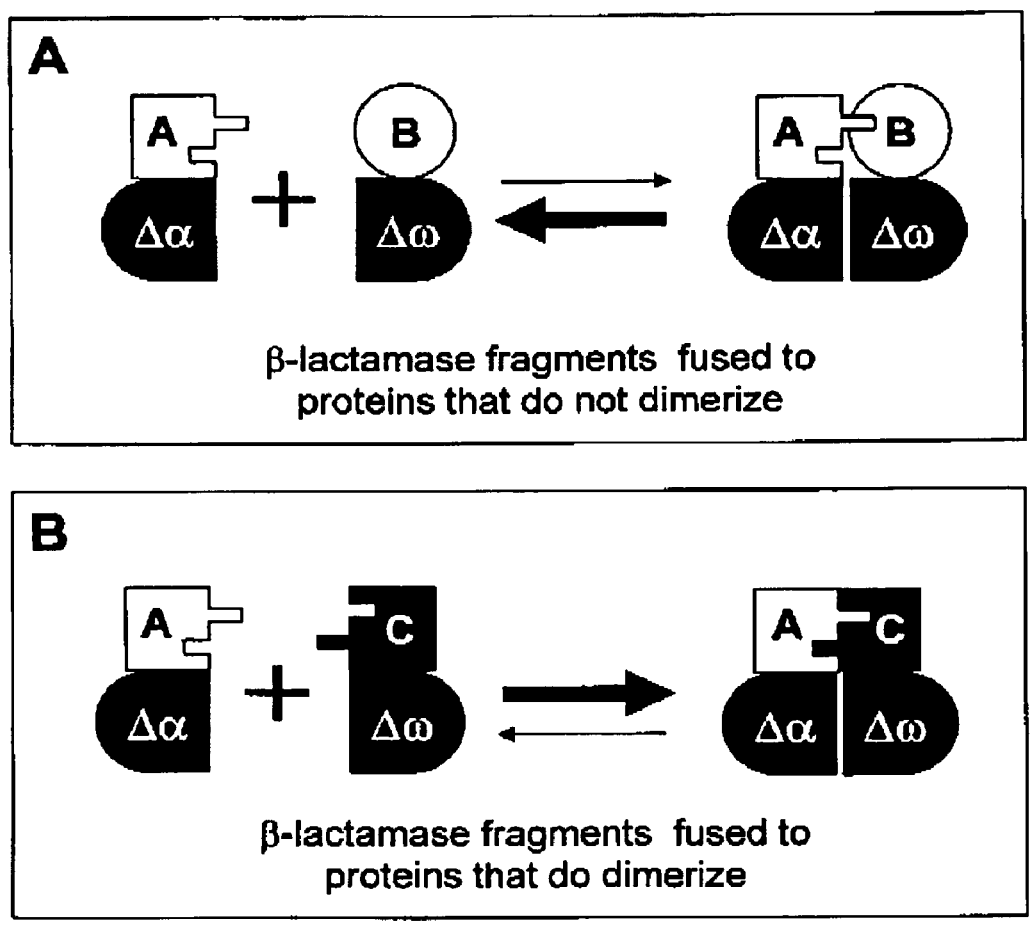
FIG. 1 schematically depicts a protein complementation assay according to the invention.

Protein fragment complementation assays (PFCA) are used to study protein-protein interactions in vitro or in vivo. Protein fragment complementation involves fusing weakly complementing fragments of the same enzyme to binding proteins of interest. The interaction of the fusion proteins is monitored by enzymatic activity of the reconstituted fragments in eukaryotic cells. In theory, the non-enzymatic components of the fusion proteins force the physical interaction of the enzymatic fragments. Thus the complementation of enzymatic fragments does not drive, but rather monitors the interaction of other proteins (FIG. 1). When β-lactamase fragments, Δα and Δω, with a breakpoint at glutamic acid 172 are fused to proteins that do not dimerize, their association is not favored and β-lactamase activity is not detected, as shown in FIG. 1A. When the Δα and Δω β-lactamase fragments are fused to proteins that can dimerize, the formation of active β-lactamase is favored, as shown in FIG. 1B.

The protein fragment complementation assays of the invention have widespread potential for understanding biological processes as they can be adapted to high-throughput assays, cDNA screens, and the study of inducible protein interactions. Such biosensors of protein-protein interactions should be invaluable in elucidating signal transduction pathways in specific cells (transformed, differentiated, dividing) in response to well defined extracellular stimuli such as hormones, cytokines and calcium. Moreover, they can be used to screen for molecules that promote or disrupt such interactions, which could serve not only as invaluable biological tools but also be applied to drug discovery.

Although several systems have been developed that use chimeras of proteins of interest and enzyme fragments to assess protein interactions, each has its limitations. For example, in mammalian cells the fluorescent signal generated by complementation of dihydrofolate reductase is not amplified enzymatically; thus, only small increments in fluorescence are achieved (Remy, I. & Michnick, S. W. (1999) *Proc Natl Acad Sci USA* 96, 5394-9; Remy, I., Wilson, I. A.& Michnick, S. W. (1999) *Science* 283, 990-3). The β-galactosidase system benefits from enzymatic amplification of its signal; however, the active enzyme is a homotetramer, and the individual fragments are large (80 kDa), making it likely that some interactions may be sterically hindered (Blakely, B. T., Rossi, F. M., Tillotson, B., Palmer, M., Estelles, A. & Blau, H. M. (2000) *Nat Biotechnol* 18, 218-22; Rossi, F., Charlton, C. A. & Blau, H. M. (1997) *Proc Natl Acad Sci USA* 94, 8405-10).

The small size, monomeric nature, and availability of a cell-permeable fluorescent substrate suggested that a mammalian system based on the β-lactamase enzyme had the potential to overcome many of the limitations of existing systems. Indeed, the β-lactamase complementation system described here exhibits an extremely high signal to noise ratio measured in mammalian cells by flow cytometry and fluorescence imaging. In addition, the ability to generate signal within minutes and the capacity to perform the assay in the absence of de novo protein synthesis suggests that this system may be ideal for studying inducible and transient protein-protein interactions in any cell type.

The β-lactamase System

β-lactamase fragment complementation seeks to overcome the limitations of the other protein fragment complementation systems in mammalian cells. TEM-1 β-lactamase is a well-characterized class A β-lactamase, which confers resistance to ampicillin by hydrolysis of the beta-lactam ring. Chaibi, E. et al. (1999) *J Antimicrob. Chemother.* 43, 447-458. The TEM-1 β-lactamase of *E. coli* is the 264 amino acid product of the ampicillin resistance gene of plasmid pBR322. TEM-1 is the archetype member of homologous Class A β-lactamases, or penicillinases.

A β-lactamase system was disclosed in U.S. patent application Ser. No. 09/526,106. This system was comprised of fragments corresponding to breakage of the full-length polypeptide chain at Glu197 (Glu172 of the mature protein). Further, the system comprised a tripeptide, AsnGlyArg (NGR), inserted between the carboxyl terminus of the Δω fragment and the linker. This peptide was selected from a random peptide library for its ability to preferentially enhance the activity of the enzyme when reconstituted from fragments fused to interactors.

In this invention, this system was applied to a mammalian cell assay system, specifically the FKBP12/FRAP/rapamycin system. Enhanced complementation observed for the β-lactamase system in the presence of the NGR peptide led to the applicability of the system in assaying protein interactions in mammalian cells. Utilizing the inducible FKBP12-FRB dimerization system, it is not only possible to monitor an inducible interaction in mammalian cells using β-lactamase complementation, but also that this assay yields a very robust signal of 50-100 fold increase in fluorescence from the responding cell population. This finding, as well as the negligible background observed from the expression of the fusion proteins in the absence of a dimerizing agent, makes the highly sensitive measurement of protein interactions using this system readily apparent.

Properties inherent to the β-lactamase system suggest that it approaches a physiologically relevant measure of protein interactions in mammalian cells. The α197 fragment is ~19 kDa whereas the ω198 fragment is only ~10 kDa. These values are both smaller than many proteins used to monitor protein localization such as green fluorescent protein, making it unlikely the fragments will significantly alter the function of the chimeric proteins being analyzed. The assay can be performed in any cell type and can be used to assay dimerization irrespective of protein localization. In addition, the system allows detection of interactions in as little as 7.5 min., and that this activity can occur in the absence of de novo protein synthesis demonstrating its utility in the study of inducible or transient protein interactions.

Binding Moieties

Binding moieties which can be assayed for their binding affinity with each other in mammalian cells include any molecules capable of a binding interaction. The binding interaction between the two or more binding moieties may be either direct or in the form of a complex with one or more additional binding species, such as charged ions or molecules, ligands or macromolecules.

The binding moieties which are attached to the reporter fragment can be any of a range of different molecules including carbohydrates, lipids, proteins, and nucleic acids, as well as portions, polymers and analogues thereof, provided they are capable of being linked to the reporter fragment. Exemplary proteins include members of a signal transduction cascade, proteins regulating apoptosis, proteins that regulate progression of the cell-cycle or development of tumors, transcriptional regulatory proteins, translational regulatory proteins, proteins that affect cell interactions, cell adhesion molecules (CAMs), ligand-receptor pairs, proteins that participate in the folding of other proteins, and proteins involved in targeting to particular intracellular compartments, such as the Golgi apparatus, endoplasmic reticulum, ribosomes, chloroplasts and mitochondria.

Other exemplary proteins include protein hormones and cytokines. Cytokines include those involved in signal transduction, such as interferons, chemokines, and hematopoietic growth factors. Other exemplary proteins include interleukins, lymphotoxin, transforming growth factors-α and β, and macrophage and granulocyte colony stimulating factors. Other proteins include intracellular enzymes such as protein kinases, phosphatases and synthases.

Exemplary proteins involved in apoptosis include tumor necrosis factor (TNF), Fas ligand, interleukin-1β converting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

Binding of molecules will depend upon factors such as pH, ionic strength, concentration of components of the assay, and temperature. In the binding assays using reporter systems described herein, the binding affinity of the binding moieties in mammalian cells should be high enough to permit forced complementation between the reporter fragments. Non-limiting examples of dissociation constants of the binding moieties in an assay solution, such as a buffered system or cell interior, are on the order of less than about $10^{-8}$ M, for example, less than about $10^{-9}$ M, or optionally, between about $10^{-9}$ to about $10^{-12}$ M, depending upon the properties of the particular assay system.

Linking of the Reporter Fragment and the Binding Moiety

The reporter fragment and one or more binding moieties are generally linked either directly or via a linker, and are generally linked by a covalent linkage. For example, when the reporter fragment and the binding moiety are proteins, they may be linked by methods known in the art for linking peptides.

In one preferred embodiment, the reporter fragment and the binding moiety comprise a fusion protein including the reporter fragment which is a low binding affinity enzyme complement and the binding moiety being assayed in mammalian cells. The fusion protein can thus be expressed from an encoding nucleic acid intracellularly. This system is advantageous since it permits the detection and quantitation of protein-protein interactions in mammalian cells, based on enzymatic complementation of the low affinity reporter fragments.

For example, in the embodiment wherein chimeric fused proteins are produced intracellularly in mammalian cells, that includes one of two complementing low affinity β-lactamase segments and a "test" protein of interest, the detected β-lactamase activity due to interactions between two chimeric proteins of interest will be proportional to the strength of the interaction of the non-β-lactamase polypeptide components. Thus, the interaction is driven by the test proteins of interest, not the complementing mutants. The enzymatic activity serves as an indicator of that interaction. Another advantage of this system is that only low levels of expression of the test proteins are required to detect binding.

The fusion gene constructs preferably are constructed and transformed into mammalian cells to produce low level expression. The system then permits the monitoring of interactions in a given cell in the presence of endogenous competing protein partners, where the fusion protein will function as a "tracer" for the binding/association reaction. Such a system will not be prone to artifacts arising from overexpression of introduced proteins. Reduction in expression of fusion gene constructs can be accomplished by choice of appropriate promoters, ribosome binding sites and other regulatory elements. For example, fusion gene constructs can be introduced into vectors in which they lie upstream of an antibiotic resistance gene whose translation is regulated by the Encephalomyocarditis virus internal ribosome entry sequence (IRES), and which contain a mutation in the splice donor/acceptor sequences upstream of the ATG sequence responsible for translational initiation of the fusion gene. This type of construct results in a lower translation efficiency of the first coding sequence in a bicistronic message, but does not affect translation of the second (antibiotic resistance) sequence, which is solely dependent on the IRES. As a result of these reduced levels of expression, the frequency of spontaneous interaction of reporter fragments, which is concentration-dependent, will be significantly reduced.

Expression of Fusion Proteins

The invention provides fusion proteins comprising a putative binding moiety and a low-affinity β-lactamase reporter fragment. The putative binding moiety may comprise any protein or other molecule whose ability to bind to a second molecule is to be tested. The low affinity reporter fragments comprise β-lactamase fragments capable of complementation with one another to generate β-lactamase activity.

Fusion proteins comprise a single continuous linear polymer of amino acids which comprise the full or partial sequence of two or more distinct proteins. The construction of fusion proteins is well-known in the art. Two or more amino acids sequences may be joined chemically, for instance, through the intermediacy of a crosslinking agent. In a preferred embodiment, a fusion protein is generated by expression of a fusion gene construct in a cell. A fusion gene construct comprises a single continuous linear polymer of nucleotides which encodes the full or partial sequences of two or more distinct proteins in the same uninterrupted reading frame. Fusion gene constructs generally also contain replication origins active in mammalian cells and one or more selectable markers encoding, for example, drug resistance. They may also contain viral packaging signals as well as transcriptional and/or translational regulatory sequences and RNA processing signals.

The fusion gene constructs of the invention are introduced into mammalian cells to assay for binding between the putative binding moieties encoded by the fusion gene constructs. The fusion gene constructs may also contain promoters and other transcriptional and/or translational regulatory sequences that are normally associated with the gene encoding the putative binding moiety. The fusion gene constructs may be introduced into mammalian cells by any method of nucleic acid transfer known in the art, including, but not limited to, viral vectors, transformation, co-precipitation, electroporation, neutral or cationic liposome-mediated transfer, microinjection or gene gun. Viral vectors include retroviruses, poxviruses, herpesviruses, adenoviruses, and adeno-associated viruses. Particularly preferred in the present invention are retroviral vectors, which are capable of stable integration into the genome of the host cell. For example, retroviral constructs encoding integration and packaging signals, drug resistance markers and one or more fusion genes of interest are useful in the practice of the invention.

Different fusion gene constructs encoding unique fusion proteins may be present on separate nucleic acid molecules or on the same nucleic acid molecule. Inclusion of different fusion gene constructs on the same nucleic acid molecule is advantageous, in that uptake of only a single species of nucleic acid by a mammalian cell is sufficient to introduce sequences encoding both putative binding partners into the cell. By contrast, when different fusion constructs are present on different nucleic acid molecules, both nucleic acid molecules must be taken up by a particular mammalian cell for the assay to be functional. Thus, problems of cell mosaicism are avoided when both fusion gene constructs are included on the same nucleic acid molecule.

The fusion gene constructs or fusion proteins of the invention may be introduced into cultured mammalian cells, mammalian cells in vivo, or mammalian cells ex vivo in which it is desired to study protein-protein interactions.

Assays

The reporter systems disclosed herein may be used to assay binding interactions of putative binding moieties attached to low affinity reporter fragments through complementation between the low affinity reporter fragments which produces a detectable signal. In addition to testing for direct binding interactions between the putative binding moieties, interactions dependent upon one or more additional molecules or ions may be evaluated. Further, biomolecular interactions in living animal cells can be evaluated, as well as the influence of various drugs, peptides and pharmaceuticals on these interactions.

In one embodiment, the binding affinity of one or more putative binding moieties may be measured by providing a reporter system including one component having one of the moieties bound to a low affinity β-lactamase reporter fragment and at least one other component including one other putative binding moiety bound to a second low affinity β-lactamase reporter fragment. The binding moieties may be different or the same. In the system, the β-lactamase reporter fragments are capable of binding and generating a detectable signal only if they are brought into proximity by the binding of the one or more putative binding moieties. The signal can be directly or indirectly detected and quantitated.

In one embodiment of the invention, protein-protein interactions can be detected and quantitated. The signal produced by the complementing reporter fragments can serve as an indicator of binding between the putative binding moieties, either directly or indirectly via a third substance. Signals which could be detected include light emission and absorbance. Exemplary signals include chromogenic, fluorescent and luminescent signals. These signals can be detected and quantitated visually or through the use of spectrophotometers, fluorimeters, microscopes, scintillation counters or other instrumentation known in the art.

Binding of components of the reporter systems disclosed herein will depend upon factors such as pH, ionic strength, concentration of components of the assay, and temperature. Assay solutions can be designed and developed for a particular system. The reporter systems disclosed herein can be used to conduct assays in systems, such as buffered cell free extracts of mammalian cells, cell interiors, solutions of cells, solutions of cell lysates, and solutions of cell fractions, such as nuclear fractions, cytoplasmic fractions, mitochondrial fractions, and membrane fractions. Methods for preparing assay solutions, such as enzyme assay solutions, cell extracts, and cell suspensions, known in the art may be used. For example, physiologically compatible buffers such as phosphate buffered saline may be used. See for example, the series entitled Methods in Enzymology, Academic Press, New York.

In one embodiment, the low affinity β-lactamase reporter fragments are capable of complementing one another to form an enzymatically active complex that is capable of catalyzing the conversion of a substrate to a product which is detectable, either directly or indirectly. In one embodiment, the β-lactamase reporter system can include two or more components, each of which is a fusion protein, wherein the fusion proteins each comprise a putative binding protein fused to a low affinity β-lactamase reporter fragment. Thus, nucleic acids encoding the fusion proteins can be constructed, introduced into cells and expressed in cells. Alternatively, the bound β-lactamase reporter units or bound binding moieties can be detecting by detecting the binding of a labeled specific binding moiety such as an antibody to the bound complex.

In one embodiment, the low affinity reporter β-lactamase subunits may be complementing subunits of β-lactamase which are required to associate in order to produce a detectable β-lactamase activity. Methods for detecting the reaction products of active β-lactamase that have been developed in the art may be used. For example, β-lactamase activity may be measured by a range of methods including live-cell flow cytometry and histochemical staining with a chromogenic substrate, such as nitrocefin. Nitrocefin is a cephalosporin which serves as a chromogenic substrate for β-lactamase. Hydrolysis of nitrocefin converts this compound from a yellowish to a pinkish color. U.S. Pat. No. 5,955,604 (Tsien et al.) discloses fluorescent substrates of β-lactamase and is incorporated herein in its entirety.

Vital substrates for β-lactamase, which can be used in mammalian cells, are also encompassed by the invention. For example, CCF2/AM can be used for live cell sorting of cells expressing β-lactamase.

Detection of Binding Events

The methods disclosed herein enable the detection and quantitation of binding events in cell lysates, as well as in intact mammalian cells. Thus, interactions between fully folded proteins are detectable, and co-translational expression of the binding moieties is not necessary for binding to be detected. In the practice of the invention, the reaction product may be detected indirectly, for example, through immunological techniques, such as immunofluorescent labeling.

Fluorescence imaging has been used to study the intracellular biochemistry of mammalian cells. A fluorescent indicator for the adenosine 3',5'-cyclic monophosphate (cAMP) signaling pathway has been described in which the sensor is a cAMP kinase in which the catalytic and regulatory subunits each are labeled with a different fluorescent dye, such as fluorescein or rhodamine, capable of fluorescence resonance energy transfer in the holoenzyme complex. A change in shape of the fluorescence emission spectrum occurs upon cAMP binding, and therefore activation of the kinase can be visualized in cells microinjected with the labeled holoenzyme. Adams et al., Nature, 349: 694-697 (1991). This system is limited by the fact that it requires microinjection, and a preferred distance between the labeled units for energy transfer to occur.

Substrates for β-lactamase have been described in the art which include a fluorescent donor moiety and a quencher, which include an attached group which makes them permeable through mammalian cell membranes, wherein the attached group is hydrolyzed off after the substrate enters the cell. Fluorescence energy transfer between the donor and quencher is monitored as an indicator of β-lactamase activity. This system also can be used in a reporter gene assay using cells containing β-lactamase reporter genes functionally linked to a promoter. Substrates for β-lactamase are described in WO 96/30540 published Oct. 3, 1996, and U.S. Pat. No. 5,955,604 the disclosures of which is incorporated herein.

Protein-protein interactions can be measured in a mammalian cell reporter system which includes one or more fusion proteins. The fusion proteins each include a putative binding protein coupled to a low affinity β-lactamase reporter fragment. For intracellular expression of the fusion proteins, one or more fusion gene constructs are prepared which include sequences encoding the fusion protein(s). The fusion gene constructs may be introduced into mammalian cells by methods available in the art, including, but not limited to, viral vectors, transformation, co-precipitation, eclectroporation, neutral or cationic liposome-mediated transfer, microinjection or gene gun.

A variety of cell-based assays can be conducted using the cells containing the fusion gene constructs. Binding of the putative binding moieties on the fusion proteins expressed in the cells can be confirmed by detecting the signal produced by the β-lactamase reporter fragments undergoing forced complementation.

The fusion gene constructs may also contain promoters and other transcriptional and/or translational regulatory sequences that are normally associated with the gene encoding the putative binding moiety. This permits the study of physiologically-relevant levels of the putative binding proteins in vivo, in contrast to systems in which test proteins are overexpressed. Further, this permits the study of naturally-occurring changes in levels of binding activity over time and can reveal the effects of endogenous or exogenous substances on binding interactions.

The methods and compositions of the invention can also be used to study other molecules which influence the interaction of two putative binding partners in mammalian cells. Proteins, peptides, nucleic acids, carbohydrates, lipids, ions, small molecules, synthetic compounds or other substances (either endogenous to the cell or exogenously added) may act as either agonists or antagonists of a binding interaction. By measuring the effect of such molecules on, for example, β-lactamase activity produced by mammalian cells containing two or more fusions representing a particular pair of test proteins, agonist or antagonist activity of such molecules can be determined. Use of the methods and compositions of the invention will allow high-throughput assays to be carried out to test for agonists or antagonists of a particular binding interaction. Such high-throughput assays will be especially valuable in screening for drugs that influence medically-relevant protein-protein interactions.

Putative binding partners, or putative binding moieties, according to the invention, can include molecules which do not normally interact with each other, but which each interact with a third molecule such that, in the presence of the third molecule, the putative binding partners are brought together. Thus, substances which influence an interaction between putative binding partners include those which stimulate a weak interaction between putative binding partners, as well as one or more molecules which mediate interaction between molecules which do not normally interact with each other. In addition, substances which influence an interaction between putative binding partners can include those which directly or indirectly affect an upstream event which results in association between the putative binding partners. For example, if phosphorylation of one of the putative binding partners endows it with the capacity to associate with another of the putative binding partners; substances which influence the interaction of the putative binding partners include those which directly or indirectly affect a kinase activity.

Assays can be developed for mammalian cells as disclosed herein to examine the effect on intermolecular interactions of a variety of compositions including drugs such as antipyretic and anti-inflammatory drugs, analgesics, antiarthritics, antispasmodics, antidepressants, antipsychotics, tranquilizers, antianxiety drugs, narcotic antagonists, anti-Parkinsonism agents, cholinergic antagonists, chemotherapeutic agents, immunosuppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins.

Protein-protein interactions mediated by a third molecule can be detected and quantitated in mammalian cells. The kinetics of binding also can be studied. Such systems are described in Examples 1-4 below, wherein β-lactamase fusion proteins are used to monitor the rapamycin-mediated interaction of the FKBP12 and FRAP proteins. Belshaw, P. J. et al., *Proc. Natl. Acad. Sci. USA*, 93: 4604-4607 (1996); Brown et al., *Nature* 369: 756-758 (1994); Chen, et al., *Proc. Natl. Acad. Sci., USA*, 92:4947-4951 (1995); and Choi, J. et al, *Science*, 273:239-242 (1996). For example, kinetics of binding can be determined by measuring β-lactamase activity at different times following addition of rapamycin to cultures of cells expressing fusions of FKBP12 and FRAP to two complementing, low affinity β-lactamase fragments (e.g., Δα and Δω). A dose-response curve can also be obtained, in which the extent of binding, as measured by β-lactamase activity, is determined as a function of rapamycin concentration.

The reporter system can also be designed with controls to permit the quantitation of the expression level of the β-lactamase fusion proteins in mammalian cells. This will make it possible to control for potential differential expression of the two (or more) fusion proteins. For example, a peptide tag for which well-characterized monoclonal antibodies are available may be fused in frame at the C-terminus of each β-lactamase fragment. Different tags, such as flag and myc may be used for Δα and Δω, to allow differential detection of the two mutants even when coexpressed in the same cells. In parallel with the determination of β-lactamase activity in the lysates of these mammalian cells, an ELISA assay can determine the precise amount of each β-lactamase fusion protein in the same lysates. First, a polyclonal anti-β-lactamase antiserum may be used to immobilize the antigens. Then the monoclonal antibody directed against the appropriate tag followed by an enzyme-linked anti-mouse secondary antibody may be used to quantify the amount of the β-lactamase fusion protein of interest. Such an approach, employing well-characterized techniques, should allow a determination of the expression levels of each fusion protein. This modification will be useful where the attached tag does not impair the binding of the protein or the ability of the reporter fragments to complement.

Applications of the Invention

As will be apparent to one of skill in the art, the invention allows a broad range of studies of protein-protein and other types of multi-molecular interaction to be carried out quantitatively or qualitatively in mammalian cells. In what follows, non-limiting examples of different applications of the invention are provided.

The observation that levels of β-lactamase activity in the presence and absence of forced complementation can be distinguished by FACS (FIG. 2), suggests that the methods of the invention can be used to screen for new binding partner(s) for a given target protein in mammalian cells. In this embodiment, the target protein, fused to a weakly-complementing β-lactamase fragment is stably expressed in a well-characterized mammalian cell line. Expression libraries containing cDNAs fused to a weakly-complementing β-lactamase mutant are introduced into these cells using, for example, retroviral vectors (e.g., Kitamura et al., *Proc Natl. Acad. Sci. USA* 92:9146-9150 (1995)) or any other means of gene transfer known in the art. Vectors expressing gene products that interact with the target protein are isolated by identifying β-lactamase-positive clones. An advantage of this system is that the screen can be carried out in any type of mammalian cell, regardless of the cell's milieu of endogenous (and potentially competing) proteins. A further possibility for this type of system is that the target protein can be localized to a specific cellular compartment, with the aim of identifying proteins involved in interactions restricted to that particular location.

The assays and methods of the invention can also be carried out in the presence of extracellular signaling molecules, growth factors or differentiation factors, peptides, drugs or synthetic analogs, or the like, whose presence or effects might alter the potential for interaction between two or more given proteins in a particular mammalian cell type.

Detection of molecular interactions, using the methods and compositions of the invention, is not limited to those occurring in the nucleus, nor is it limited to intracellular interactions in mammalian cells. For instance, interactions involving surface receptors can be detected in the practice of the invention. In one embodiment, the invention provides new techniques for detecting ligand-induced dimerization of surface receptors in mammalian cells. Dimerization, or higher order oligomerization, of cell surface receptors is often a prerequisite for receptor activation and ensuing signal transduction. For example, the binding of epidermal growth factor (EGF) to its receptor stabilizes the dimerization of the receptor and leads to activation of its tyrosine kinase activity. Schlessinger et al. (1992) *Neuron* 9:383-391; Ullrich et al. (1990) *Cell* 61:203-212; and Weiss et al (1997) *Curr. Opin. Genet. Dev.* 7:80-86. Example 11, infra, discloses the use of β-gal complementation to monitor membrane receptor dimerization in mammalian cells.

By combining the methods and compositions of the invention with state-of-the-art methods for construction of high-titer, high-complexity cDNA libraries in retroviruses (e.g., Pear et al., (1993) *Proc. Natl. Acad. Sci. USA* 90:8392-8396), it will be possible to identify interaction partners of a specific test protein in mammalian cells (i.e., perform functional genomics at the protein level). For this application, construction of cDNA libraries in retroviral vectors wherein the cDNA coding sequence is fused to a sequence encoding a low affinity β-lactamase reporter fragment will be used. A sequence encoding a binding protein of interest will be fused to a low affinity β-lactamase reporter fragment in a first retroviral vector. In a second series of retroviral vectors, a second complementing low affinity reporter β-lactamase subunit will be fused to a variety of different proteins that will be tested for their ability to bind to the protein of interest. Testing will be conducted by co-infection of mammalian cells with the first and one of the series of second retroviral vectors. Those test proteins which are capable of binding to the protein of interest will allow detection of a reporter signal in cells in which they are co-expressed with the protein of interest. This application will also be useful in screening for agonists and antagonists of medically-relevant protein interactions.

The use of fluorescence-activated cell sorting techniques is particularly well-suited to this embodiment of the invention. For example, β-lactamase-positive mammalian cells which contain cDNAs expressing gene products that interact with the target protein will generate a signal that will allow such cells to be purified by cell-sorting techniques. Such cDNAs could be delivered, for example, using retroviral vectors that allow introduction of high complexity cDNA libraries with high infection efficiency.

In one embodiment of the invention, mammalian cells in which a protein encoded by one of the series of second vectors is able to interact with the binding protein of interest encoded by the first vector are detected and isolated by flow cytometry or fluorescence-activated cell sorting (FACS). Methods for flow cytometry and FACS are well-known in the art; e.g., Nolan et al. (1988) *Proc. Natl. Acad. Sci. USA* 85:2603-2607; Webster et al., *Exp. Cell Research,* 174:252-265 (1988); and Parks et al. (1986) in *The Handbook of Experimental Immunology,* (eds. Weir, D. M., Herzenberg, L. A., Blackwell, C. C. & Herzenberg, L. A.), Blackwell, Edinburgh, 4th edition, pp. 29.1-29.21. In this way, clones of cells in which binding occurs can be isolated and propagated for further study. This aspect is particularly suited for studies of developmental mechanisms, wherein it is possible to select a population of mammalian cells in which a particular developmentally-relevant interaction has occurred and study the further development of that cell population, while at the same time, studying the further development of the cells in the population in which the interaction has not occurred, for comparison. In a similar fashion, the practice of the invention makes it possible to isolate and/or study the further development of mammalian cells exhibiting interactions involving protein such as transcriptional regulatory proteins, translational regulatory proteins, DNA replication proteins, mRNA splicing proteins, proteins involved in signal transduction, proteins involved in cell-cell and cell-substrate adhesion (for example, cell movement, axon guidance and angiogenesis), oncogene products, tumor suppressors, proteins involved in cell-cycle control and viral proteins, such as those involved in regulation of viral replication, virus-host interactions and virus assembly, and proteins which are subunits, crosslinkers, modifying agents or molecular motors within the cytoskeleton of cells.

For a given target protein whose gene is capable of being fused to a low-affinity complementing reporter β-lactamase subunit, it is possible to identify known and heretofore unknown proteins or other endogenous or extraneous substances with which it interacts, by using the compositions and methods of the invention. In like manner, for a sequence which encodes a protein of unknown function, such as may be obtained from a nucleic acid sequence database, (or a plurality of sequences such as a cDNA library) the practice of the invention allows one to identify molecules with which the encoded protein interacts. The identity of the interacting molecule(s) is likely to provide information with respect to the structure and/or function of the unknown protein. Thus, the practice of the invention will likely aid in the identification and characterization of newly-discovered proteins and protein-coding nucleic acid sequences.

In another aspect of the invention, a shotgun approach to the identification of protein-protein interactions can be taken by generating a first set of constructs which will express the encoded products of one cDNA library fused to a first low-affinity complementing β-lactamase subunit and a second set of constructs which will express the encoded products of a second (or the same) cDNA library, fused to a second low-affinity complementing β-lactamase subunit. Co-expression of the two sets of constructs and selection of cells in which complementation occurs will allow the isolation of clones and the identification of cDNAs which encode interacting partners. One or both of the interacting partners may be known; alternatively, both of the interacting partners may represent heretofore unidentified proteins. If both partners are known, new information about their binding specificity may be obtained. If one partner is known, it may provide information on the function of the unknown binding partner. If neither are known, the observation that they interact may assist in the eventual identification of one or both of the interacting pair.

The invention may be applied to studies of the mechanisms that regulate either homo- or hetero-dimerization of specific molecules, including high efficiency screening to identify synthetic or naturally occurring compounds capable of influencing such dimerization.

The invention can be used for investigations relating to the localization of specific complexes within intact mammalian cells, or intact animals. Types of mammalian cells which can be used are primary or established cell lines and other types of embryonic, neonatal or adult cells, or transformed cells (for example, spontaneously- or virally-transformed). These include, but are not limited to fibroblasts, macrophages, myoblasts, osteoclasts, osteoclasts, hematopoietic cells, neurons, glial cells, primary B- and T-cells, B- and T-cell lines, chondrocytes, keratinocytes, adipocytes and hepatocytes.

It is also possible, through practice of the invention, to devise systems for regulation of enzyme activity by regulating the association of complementing β-lactamase fragments in a mammalian cell. This aspect of the invention has potential applications to human therapy, as a method to regulate the enzyme-driven conversion of pro-drugs into their active forms.

Processes involving molecular interactions, particularly protein-protein interactions, which can be studied in the practice of the invention include, but are not limited to, transcription, translation, replication, mitosis, growth control, progression and regulation of the cell-cycle, apoptosis, cell-cell, cell-substratum and cell-ligand interactions, intracellular signal transduction cascades, oncogenesis, cell lineages, and embryonic development. Examples of cell ligands include leptin and growth factors such as epidermal growth factor (EGF), nerve growth factor (NGF), platelet-derived growth factor (PDGF), and insulin-like growth factors I and II (IGF-I and IGF-II), transforming growth factors α and β (TGF-α and TGF-β), endorphins and endorphin receptors, prostaglandins and their receptors, cytokines and their receptors, neurotransmitters and their receptors, adrenergic receptors, and cholinergic receptors. Receptors which could interact with ligands include EGF, NGF, and PDGF receptors and leptin receptors.

Additional interactions that can be studied by the practice of the invention include interactions involved in cell metabolism and cell structure. These include, but are not limited to, interactions that are involved in energy metabolism or which establish or modify the structure of the membranes, cytoplasm, cytoskeleton, organelles, nuclei, nuclear matrix or chromosomes of cells. Interactions among constituents of the extracellular matrix, or between constituents of the extracellular matrix and cells, can also be studied with the methods and compositions of the invention.

The invention will be further understood by the following non-limiting examples.

EXAMPLES

Example 1

Inducible β-Lactamase Complementation in Mammalian Cells

Figure 2:
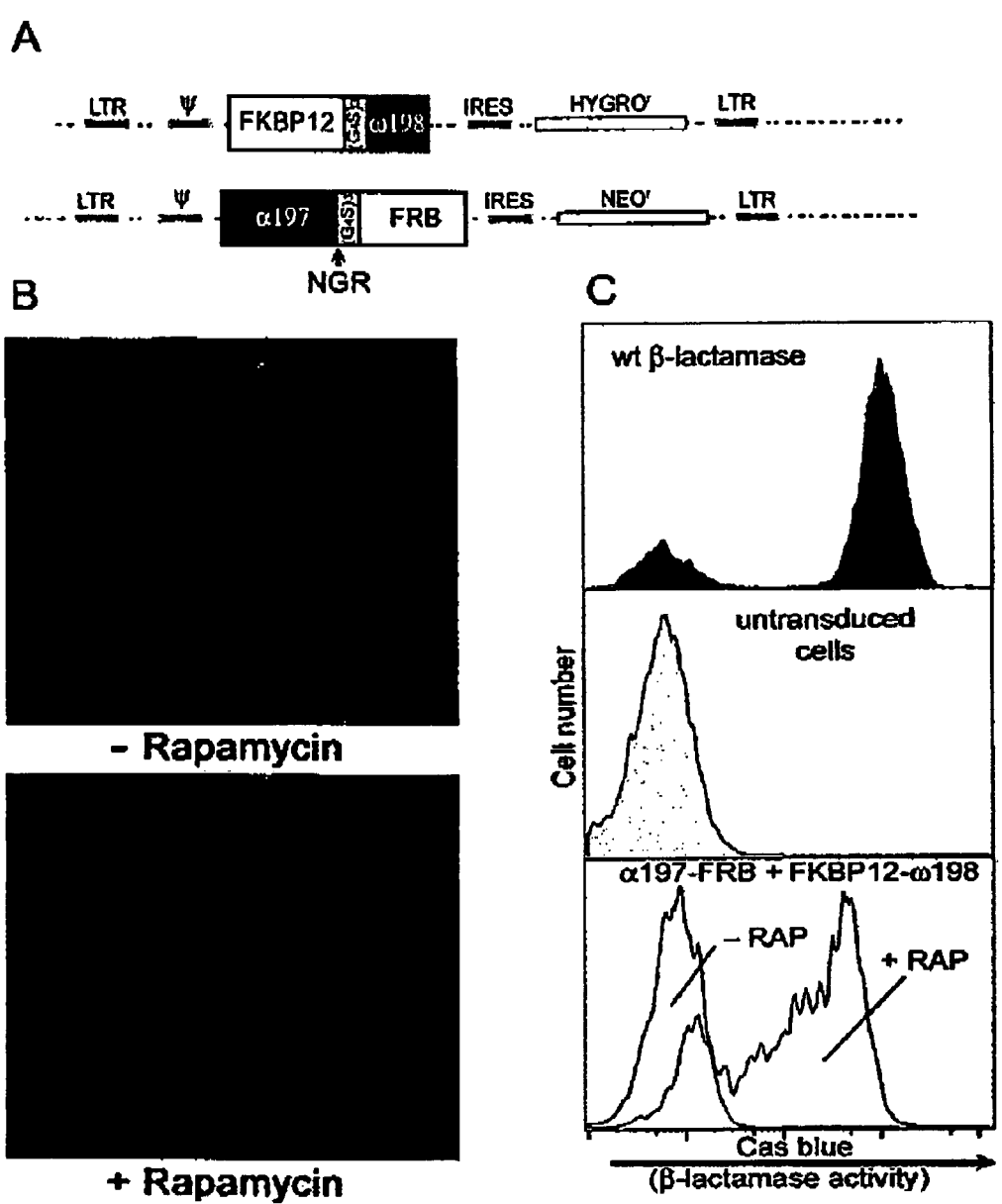
FIG. 2 shows inducible β-lactamase fragment complementation in C2C12 myoblasts.

A reporter system using β-lactamase complementation to evaluate protein-protein interactions was constructed. Experiments were designed to test whether the β-lactamase fragments in conjunction with the NGR peptide could be used to monitor an inducible protein interaction in mammalian cells (FIG. 2). The well characterized inducible interaction of FKBP12 and FRB was used as a model system (Chen, J., Zheng, X. F., Brown, E. J. & Schreiber, S. L. (1995) *Proc Natl Acad Sci USA* 92, 4947-51; Brown, E. J., Albers, M. W., Shin, T. B., Ichikawa, K., Keith, C. T., Lane, W. S. & Schreiber, S. L. (1994) *Nature* 369, 756-8; Ho, S. N., Biggar, S. R., Spencer, D. M., Schreiber, S. L. & Crabtree, G. R. (1996) *Nature* 382, 822-6; Belshaw, P. J., Ho, S. N., Crabtree, G. R. & Schreiber, S. L. (1996) *Proc Natl Acad Sci USA* 93, 4604-7; Choi, J., Chen, J., Schreiber, S. L. & Clardy, J. (1996) *Science* 273, 239-42; the disclosures of which are incorporated herein). FKBP12 (FK506 Binding Protein 12) binds FRB (the FKBP12 binding domain of FRAP) only in the presence of the pharmacological agent rapamycin, an interaction that increases with the dose of rapamycin. Rapamycin is a small cell permeable molecule that can be added directly to the culture medium resulting in heterodimerization of FKBP12 and FRB. Since rapamycin is unable to bind two FKBP12 molecules at the same time and FRAP only binds rapamycin within the FKBP12-rapamycin complex, only heterodimers form upon rapamycin treatment. (Ho, S. N. et al., *Nature*, 382:822-826 (1996), the disclosure of which is incorporated herein).

Two fusion proteins were constructed using flexible linkers (Gly$_4$Ser)$_3$ (SEQ ID NO: 6): (i) FKBP12 was fused to the N-terminus of the ω198 fragment and (ii) FRB was fused to the carboxy-terminus of the α197 fragment containing the NGR peptide (FIG. 2A). FIG. 2A shows a schematic of the bicistronic, retrovirally expressed fusion proteins FKBP12ω198 and α197FRB with selectable markers for hygromysin (hygro$^R$) and neomycin (neo$^R$) driven by an internal ribosome entry sites (IRES). Ψ designates the viral packaging signal and LTR marks the long terminal repeats. The bacterial signal sequence from each of the β-lactamase fusion fragments was removed. The fusion constructs were expressed using pWZL retroviral vectors that encode proteins conferring resistance to hygromycin or neomycin. The pWZL vectors were selected for use because they are expressed at relatively low levels; in these vectors the splice donor/acceptor is deleted, resulting in reduced translation efficiency in mammalian cells compared to other retroviral vectors such as MFG (Rossi, F., Charlton, C. A. & Blau, H. M. (1997) *Proc Natl Acad Sci USA* 94, 8405-10; Riviere, I., Brose, K. & Mulligan, R. C. (1995) *Proc Natl Acad Sci USA* 92, 6733-7). Thus, these vectors avoid vast overexpression of proteins and more closely approximate physiological levels.

A stable cell line, containing the FKBP12ω198-hygro and α197FRB-neo constructs, was established through retroviral infection of mouse myoblast C2C12 cells, and subsequent antibiotic selection. Cells from this population were treated with 50 nM rapamycin for 2 hours and assayed for β-lactamase activity using the fluorogenic CCF2/AM substrate (Zlokarnik, G., Negulescu, P. A., Knapp, T. E., Mere, L., Burres, N., Feng, L., Whitney, M., Roemer, K. & Tsien, R. Y. (1998) *Science* 279, 84-8). The intact CCF2/AM substrate when excited by a UV wavelength of 409 nm emits at 520 nm (green), whereas upon cleavage by β-lactamase it emits at 447 nm (blue). FIG. 2B shows an immunofluorescence assay of β-lactamase activity. C2C12 cells expressing the FKBP12ω198 and α197FRB fusions were loaded with the cell permeable CCF2/AM substrate, in the absence (upper panel) and presence (lower panel) of rapamycin (2 hours), and then imaged by fluorescence microscopy. Green is indicative of intact substrate, whereas blue indicates cleaved substrate. As shown in FIG. 2B (upper panel), the cells expressing the fusion proteins appear green in the absence of rapamycin, indicating that little or no cleavage of the substrate has occurred. However, upon exposure to rapamycin the substrate is cleaved, shifting the fluorescence from green to blue indicating reconstitution of β-lactamase activity (FIG. 2B, lower panel). These results revealed that inducible dimerization of FKBP12 and FRB could lead to the complementation of the β-lactamase fragments resulting in functional β-lactamase activity in mammalian cells.

These data were confirmed by performing a quantitative measurement of β-lactamase activity by flow cytometry (FACS) using the CCF2/AM substrate (FIG. 2C). FIG. 2C shows a FACS analysis of β-lactamase activity. Cells with and without rapamycin treatment (2 hours) were trypsinized, loaded with CCF2/AM substrate and assayed by flow cytometry. Increases in cascade blue fluorescence are indicative of β-lactamase activity (log scale). Upper panel—β-lactamase staining of cells expressing wild-type β-lactamase; middle panel—untransduced cells stained with the CCF2 substrate; lower panel—cells expressing the β-lactamase fusion constructs with and without rapamycin. Dimerization of the fusion constructs induced by rapamycin causes a 50-100 fold increase in cascade blue fluorescence from the responding population. The histograms of the cells that stably expressed FKBP12ω198 and α197FRB in the absence of rapamycin (lower panel) overlapped with and were not significantly different from untransduced negative control cells (middle panel). By contrast, following exposure of the cells harboring the β-lactamase fragments to rapamycin for 2 hours, enzyme activity was substantially induced and an increase in fluorescence of 50-100 fold above background was evident. Two features of these data are particularly noteworthy: (1) the almost undetectable background activity resulting from complementation in the absence of rapamycin and (2) the marked increase (orders of magnitude) in the signal generated by the complementation.

In this experiment, 20% of the cells expressing wild-type β-lactamase did not stain positive for β-lactamase activity even though the cells were kept in continuous drug selection to ensure retention of the virus containing the wild-type β-lactamase gene. A similar percentage of non-responding cells (~23%) can be seen in the population of cells expressing the chimeric β-lactamase proteins in the presence of rapamycin either by flow cytometry or fluorescence imaging. This phenomenon was also noted in the original study describing the CCF2/AM substrate with similar ratios, 80% responding and 20% not responding, suggesting that this may be a feature of the substrate staining procedure itself (Zlokarnik, G., Negulescu, P. A., Knapp, T. E., Mere, L., Burres, N., Feng, L., Whitney, M., Roemer, K. & Tsien, R. Y. (1998) *Science* 279, 84-8).

Example 2

Time Course of Inducible β-Lactamase Complementation in C2C12 Myoblasts

Figure 3:
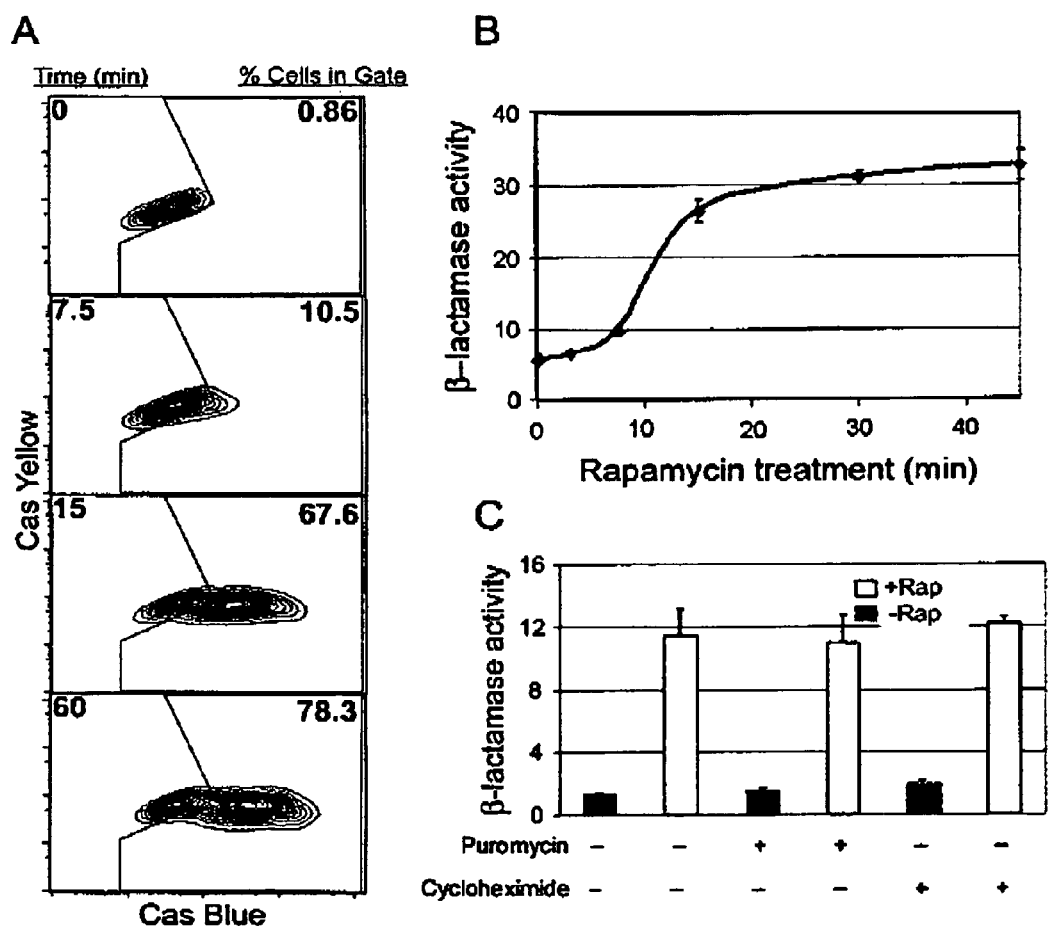
FIG. 3 shows a time course of inducible β-lactamase complementation in C2C12 myoblasts.

FIG. 3A shows a time course of rapamycin treatment in C2C12 cells expressing the chimeric β-lactamase fusion proteins that demonstrated the ability to distinguish quantitatively the responding from the non-responding population. The FKBP12ω198-α197FRB cell line was assayed for β-lactamase activity by FACS. Cells were stained with the CCF2/AM substrate, treated with rapamycin, and assayed over time. In FIG. 3A, the gate is represented in the center of each plot and the percentage of cells falling within this region are shown in red. When a gate was drawn around the cells expressing the fusion constructs prior to induction (time zero), it only included 0.9% of the cells. Notably, 10% of the cells were positive at 7.5 min after rapamycin addition, and at one hour 76% of the population stained positive for β-lactamase activity, i.e., most if not all, of the cells capable of responding. Longer rapamycin treatment did not significantly increase the numbers of positive cells.

The time course was rapid and began to plateau within 15 min. This is most clearly evident when the data from a FACS analysis performed in triplicate are presented as mean fluorescence (FIG. 3B). FACS data (from A) represented as mean cascade blue fluorescence were calculated in triplicate and graphed over time. Following rapamycin addition, a response was seen as early as 7.5 min after rapamycin treatment and was 70% maximal within 15 min demonstrating that using a bulk assay for fluorescence, the generated signal is also detectable within minutes of induced complementation. These kinetics are significantly faster than those reported for other systems utilizing the FKBP12-FRB proteins to induce dimerization (Otto, K. G., Jin, L., Spencer, D. M. & Blau, C. A. (200 1) *Blood* 97, 3662-4; Muthuswamy, S. K., Gilman, M. & Brugge, J. S. (1999) *Mol Cell Biol* 19, 6845-57), which demonstrates the high specific activity of the complemented enzyme and the extreme sensitivity of the system.

The rapid kinetics of β-lactamase reconstitution upon addition of rapamycin suggested that de novo protein synthesis might not be necessary. To test this possibility, β-lactamase activity was assayed in the presence of the protein synthesis inhibitors puromycin and cycloheximide at concentrations of 100 μg/ml for 2 hours prior to the addition of rapamycin. Neither of these inhibitors significantly altered the amount of complementation observed relative to the controls, indicating that de novo protein synthesis is not necessary for β-lactamase complementation (FIG. 3C). As shown in FIG. 3C, α197FRB-FKBP12ω198 cells were treated with either puromycin or cycloheximide (100 ug/ml) for two hours before addition of rapamycin (1 hour). The cells were stained with the CCF2/AM substrate and assayed by flow cytometry. The mean fluorescence for the cascade blue channel was calculated in triplicate and graphed on the Y-axis. Many inducible protein-protein interactions have been documented to occur on a timescale of seconds to minutes. The data shown here suggest that the β-lactamase system has the potential to monitor not only rapid, but possibly also transient protein-protein interactions.

Example 3

Detection of Constrained Protein-Protein Interactions in Mammalian Cells

β-lactamase fragment complementation in an inducible protein-protein interaction in mammalian cells was carried out using fusion proteins expressed in myoblast cells. These fusion proteins were forced to interact by an inducer, and analyzed in the presence of a fluorescent substrate for β-lactamase activity. The negative control for β-lactamase activity was the same cell line expressing fusion proteins in the absence of inducer. The "signal" of β-lactamase activity of cells expressing fusion proteins that had been induced to interact was compared to the "noise" of the negative control. The positive control for β-lactamase activity was a cell line expressing wild-type β-lactamase. β-lactamase activity in cells expressing the fusion proteins was analyzed following addition of the inducer at different time points to determine the time course and maximum signal.

Figure 4:
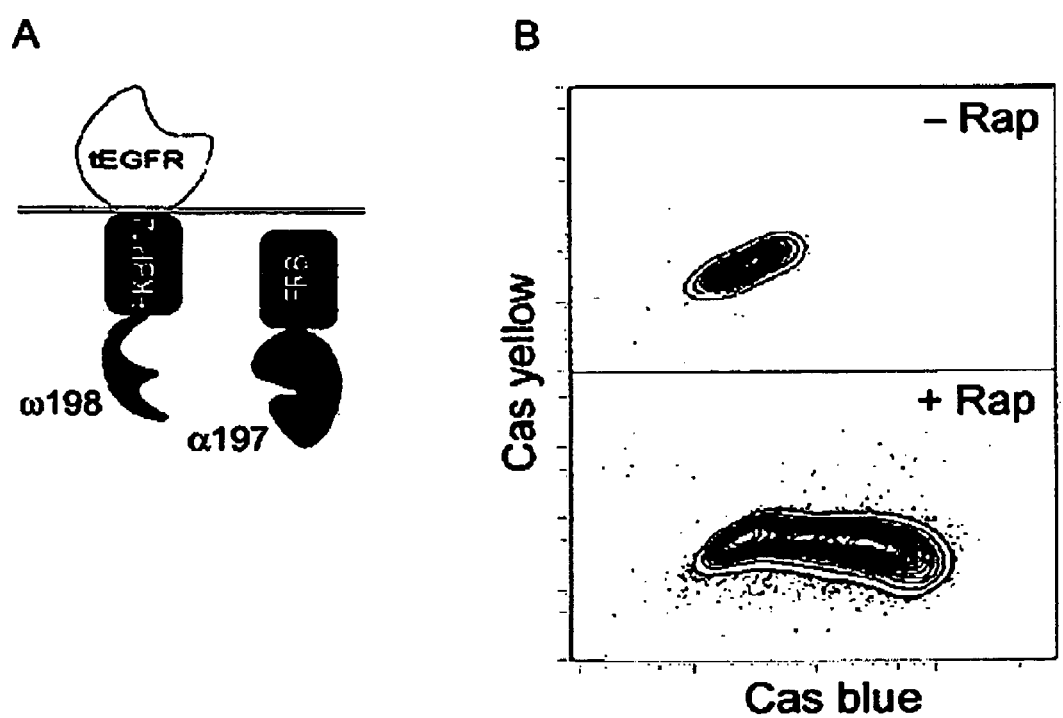
FIG. 4 shows the interaction of a membrane-bound and cytoplasmic protein assayed by β-lactamase complementation in C2C 12 myoblasts.

Cell surface mediated signal transduction events often require the interaction of a membrane associated protein, such as a transmembrane receptor with a cytoplasmic protein. In order to test whether the β-lactamase system is capable of monitoring interactions in such a constrained configuration, a model membrane bound protein was constructed that would interact with a cytoplasmic protein only in the presence of an inducer. For this purpose, a tripartite fusion construct was generated comprised of the extracellular and transmembrane regions of EGFR (tEGFR, see Blakely, B. T., Rossi, F. M., Tillotson, B., Palmer, M., Estelles, A. & Blau, H. M. (2000) *Nat. Biotechnol* 18, 218-22)) that anchored the protein to the plasma membrane fused to the FKBP12ω198 chimera (FIG. 4). FIG. 4A shows a diagram depicting the membrane-bound and cytoplasmic fusion proteins which were co-expressed in C2C12 cells. The tEGFR (truncated Epidermal Growth Factor Receptor) was used to tether the FKBP12ω198 to the plasma membrane. This fusion protein was co-expressed with a cytoplasmic α197-FRB chimera, as previously described.

Cells expressing these constructs were assayed by FACS for induction of β-lactamase activity in the presence of rapamycin (FIG. 4B). FIG. 4B shows cells expressing the fusion constructs, in the presence (upper panel) or absence (lower panel) of rapamycin (1 hour), were assayed by flow cytometry. The magnitude of β-lactamase complementation observed when proteins are in a constrained, membrane-anchored conformation is comparable to that observed when the proteins are freely expressed in the cytoplasm (compare FIG. 3A and FIG. 4B).

Example 4

Retroviral Vectors for Expression of β-Lactamase in Mammalian Cells

The β-lactamase system was combined with the FKBP12/FRAP/rapamycin system to generate mammalian cell expression systems as follows:

MMLV-based retroviral vectors with antibiotic resistance to either G418 or hygromycin were selected. Retroviral vectors were chosen because 1) they stably integrate into the DNA of mammalian cells and 2) they use a bicistronic mRNA to couple antibiotic resistance with uptake and expression of the fusion construct. The construct was a Moloney Murine Leukemia Virus (MMLV)-based retroviral vector that has been shown to efficiently transduce C2C12 myoblast cells (Kinsella, T. & Nolan, G. (1996) *Hum. Gen. Ther.* 7, 1405-1413).

To create the β-lactamase fusion proteins for retroviral expression in mammalian cells an oligonucleotide encoding a GS-linker, 5'TCGAGGGTGGAGGCGGTTCAGGCGGAG-GTGGCAGCGGCGGTGGCGGATCG G (SEQ ID NO:01), was inserted into the Xho I/Sal I site of both pWZL-neo and pWZL-hygro. The α197-NGR fragment was amplified by PCR from plasmid FHT 4002A1 using primers 5'CTCGAG-CACCCAGAAACGCTGG (SEQ ID NO:02) and 3'GTC-GACTTCCCGCCCATTTTCG (SEQ ID NO:03). The ω198 fragment was amplified by PCR using primers 5'CTCGAGG-GAGTGCAGGTGGAAACC (SEQ ID NO:04) and 3'CTC-GACTTCCAGTTTTAGAAGC (SEQ ID NO:05). The α197 fragment was cloned into the XhoI site of pWZL-GS-Neo and the ω198 fragment was cloned into the SalI site of pWZL-GS-Hygro. FRB corresponding to amino acid residues 2025-2114 of human FRAP was cloned as an XhoI/SalI fragment into the SalI site of pWZL-α197-GS-Neo. The full length coding sequence of FKBP12 was cloned as a SalI/XhoI fragment into the XhoI site of pWZL-GS-ω198-hygro. The tEGFR corresponding to AA 1-655 (Blakely, et al. (2000) *Nat Biotechnol* 18, 218-22) was cloned as an NcoI/BamHI fragment into the pWZL-FKBP12ω198-hygro vector. The wild-type β-lactamase was expressed from a pWZL vector also encoding puromycin resistance.

Example 5

Retroviral Production, Infection, and Mammalian Cell Culture

The ecotropic ΦNX packaging cell line (P. L. Achacoso and G. P. Nolan, unpublished) was transiently transfected with the proviral constructs using FuGENE transfection reagent (Boehringer Mannheim, Indianapolis, Ind.). The virus-containing supernatant from the transfected cells was removed 48-72 hours later and applied to C2C12 myoblasts cells which are a well-characterized, fast-growing cell line (Blau, H., Chiu C. & Webster, C. (1983) *Cell* 32, 1171-1180). Polybrene was added to a final concentration of 8 µg/ml (Sigma, St. Louis, Mo.). Singly and doubly infected cells were selected by antibiotic resistances. Transduced cells were selected and maintained in the appropriate antibiotic (G418, hygromycin, puromycin or neomycin; Invitrogen, Carlsbad, Calif.) at a concentration of 1 mg/mL. C2C12 myoblasts were grown in DMEM (Invitrogen) 20% FBS. Cells were treated with 50 nM rapamycin unless otherwise stated. The selected cells were expanded as populations for testing.

Example 6

β-Lactamase Assayed by CCF2/AM Staining, Immunofluorescence and FACS Analysis in Mammalian Cells The cell lines described above were assayed using a fluorescence activated cell sorter (FACS). With FACS, individual, mammalian cells can be characterized for beta-lactamase activity. Data were collected on a modified Facstar plus (Becton Dickinson, Franklin Lakes, N.J.) with MoFlo electronics (Cytomation, Fort Collins, Colo.). Cells were trypsinized, washed twice in PBS, incubated with the fluorescent substrate CCF2/AM (Aurora Biosciences, San Diego, Calif.) for 1 hour, then washed twice in a PBS 5% FBS solution. In some embodiments, 10,000 events were collected for each sample. Cells were excited with a Krypton laser (406 nm) and emission data for the samples were collected at 420-460 nm (Cascade Blue filter) and 500-590 nm (Cascade Yellow filter) using a Becton Dickinson FACS machine. A decrease in the intensity of green fluorescence and an increase in the intensity of blue fluorescence indicated β-lactamase activity. Quantification of β-lactamase activity as the ratio (mean blue fluorescence in sample cell line)/(mean blue fluorescence in negative control cell line)+/− standard deviation indicated the signal-to-noise ratio of β-lactamase fragment complementation in the system.

In an uncleaved CCF2/AM substrate, fluorescence resonance energy transfer between the donor fluorophore (coumarin), excited by an outside source, and the acceptor fluorophore (fluorescein), results in energy emission in the green portion of the spectrum. Cleavage of substrate by β-lactamase prevents excitation of the donor fluorophore by FRET and results in energy emission in the blue spectrum. The acceptor fluorophore, however, remains in the cell, and thus, would be susceptible to excitation by an outside source. Emission data from cells excited by the 407 nm Krypton laser are collected in Cascade Blue (CasB) between 420 nm and 460 nm and in Cascade Yellow (CasY) between 500 nm and 590 nm. Excitation of acceptor fluorescein (FITC) by the 488 nm Argon laser generates an emission spectra with a peak at 525 that would be collected through the CasY filter between 500 nm and 590 nm.

To assay β-lactamase in C2C12 myoblasts, the CCF2/AM substrate (Aurora biosciences, San Diego, Calif.) was used at a final concentration of 2 uM in DMEM with 2.5 mM probenecid. Cells were washed, once in PBS then incubated for 30 min with the CCF2/AM substrate at a concentration of $3 \times 10^5$ cells/ml. The plate was washed 3 times in PBS and visualized with a β-lactamase filter set (Chroma Technologies Battleboro, Vt.: excitation 405+/−10 nm, 425 dichroic mirror, 435 nm LP emission).

Example 7

Tripartite Fusions for the Quantitation of Protein-Protein Interactions

To permit protein interactions to be studied in a quantitative manner in the system described in the above Examples and to control for effects on either the binding ability of the binding moiety or the complementing ability of the reporter fragments resulting from both activities being present in a single fusion protein, additional modifications can be made to monitor the expression of the components of the system. In the above described system, the β-lactamase fusion proteins will be expressed from the same viral promoter, however, for some proteins, it is possible that their expression level will be influenced by the specific fusion partner. In particular, some proteins or domains could affect the stability or conformation of the β-lactamase domain. As a result, differences in the ability of the test proteins (the putative binding moieties) to complement one another could be observed that are not based on a physiological mechanism.

In order to avoid these problems, fusions containing three components (β-lactamase fragment, FKBP12 or FRAP, and a test protein) can be constructed. The most N-terminal component can be a test protein, followed by FKBP12-Δω or FRAP-Δα. The presence of the FKBP12 and FRAP portions would allow rapamycin-mediated dimerization of these fusions, and the efficiency of β-lactamase complementation in the presence of rapamycin would likely be dependent on the FKBP12/FRAP/rapamycin interaction. The absolute values of β-lactamase activity obtained by simple coexpression (in the absence of rapamycin) of fusions containing a fixed protein of interest and different interacting partners can be determined. In parallel samples, β-lactamase activity can be measured upon induction of complementation with a fixed amount of rapamycin. The ratio between the β-lactamase activity obtained in the absence or in the presence of rapamycin would indicate the relative ability of the different protein pairs to interact with each other. An added advantage of this approach would be that the presence of the FKBP12 and FRAP domains provide a flexible hinge between the β-lactamase fragments and the putative binding moieties that are being analyzed. This reduces the possibility of interference between β-lactamase and the proteins of interest. Furthermore, it allows direct testing of the functional integrity of the β-lactamase components in the fusions without the need for recloning into more efficient viral vectors.

tetR-FKBP12-Δω or tetR-FRAP-Δα tripartite fusions can also be used. Coexpression of these constructs, in which dimerization is driven by the tetracycline repressor (tetR) protein (Hinrichs, W. et al., *Science*, 264:418-420 (1994), the disclosure of which is incorporated herein), would yield β-lactamase positive cells. This result would indicate that functional tripartite fusions can be constructed, in which the dimerization of the most N-terminal peptide component can efficiently drive complementation of the C-terminal β-lactamase fragment polypeptides.

Example 8

Dimerization of Myogenic Regulators Using Complementing β-Lactamase Fusion Proteins The β-lactamase complementation system can be used to assay for the dimerization and nuclear translocation of HLH proteins (helix-loop-helix proteins, Murre et al. (1989) *Cell* 56:777-783) including activators of muscle-specific proteins (myoD, myogenin, myf5, MRF-4), inhibitors of myogenesis (Id, Mtwist, I-mf) and ubiquitous E2A-type proteins (E47, E12, HEB).

In a first step, a myoD-Δα-β-lactamase (myoD-Δα) fusion construct and a E12-Δω-β-lactamase (E12-Δω) fusion construct are engineered in selectable retroviral vectors, as described above for FRAP-Δα and FKBP12-Δω. The two constructs can be transduced into C2C12 myoblasts. Following selection with the appropriate drugs for cells which express both constructs, β-lactamase activity can be quantitated using the chromogenic or fluorimetric assay described above. β-lactamase activity would indicate that heterodimerization of the fusion proteins is occurring in this cell type. If β-lactamase activity is detected, individual cells can be analyzed using a fluorescent CCF2/AM stain in order to determine if the heterodimers are present in the nucleus. Wild-type β-gal can be specifically directed to and detected in the nucleus by inclusion of a nuclear localization sequence (nls) (see e.g., Hughes and Blau, *Nature*, 345:350-352 (1990)).

Inclusion of an "nls" sequence in a β-lactamase hybrid protein can allow direction and detection of the β-lactamase hybrid protein in the nucleus. Knowledge of the site of localization in the cytoplasm or nucleus would aid in assessing the function of the protein interactions, e.g. sequestration and inhibiting activity, or promoting activity. This method would permit visualization of fluorescent markers of myogenesis, such as desmin, and creatine kinase, in correlation with the localization of β-lactamase, using the sensitive CCF2/AM substrate described above.

All fusion constructs between myogenic regulators and complementing β-lactamase fragments described in the following sections may be tested in a muscle cell where heterodimerization of the endogenous myogenic regulator is known to occur. In addition, the following controls also may be performed. The myoD-Δα construct may be cotransduced into the cell with FKBP12-Δω, and the E12-Δω construct may be cotransduced with FRAP-Δα. This combination of constructs should result in no β-lactamase activity, unless some unusual mechanism exists in the particular cell type being tested that enhances complementation of the weakly complementing β-lactamase peptides independent of heterodimerization of the non-β-lactamase parts of the molecule. The FRAP-Δα and FKBP12-Δω may also be cotransduced and cells treated with rapamycin as a positive control for complementation in each cell type. Cells in high serum medium (growth medium) and cells in low serum medium (differentiation medium) should/will give different results.

Example 9

In Vivo Assay for the Effect of Growth Factors and Substrates on Heterodimerization and Homodimerization Using the constructs described above in Example 8, C2C12 myoblasts can be transduced with one of the myogenic HLH fusion constructs and the E12-Δω construct. Although C2C12 cells will already contain endogenous myogenic HLH proteins and E12, the chimeric constructs will act as a "tracer" to measure the extent of heterodimerization. Transduced cells then may be stimulated to either differentiate or proliferate by changes in serum levels or the addition of growth factors (TGF-β, bFGF, IGF-I and IGF-II) in the presence or absence of substrates such as fibronectin or laminin. β-lactamase activity can be measured as a function of time. Rapid changes in β-lactamase activity after growth factor stimulation may suggest a more direct mechanism of action of a given extracellular signal on the formation of specific heterodimers. Slower changes may indicate that the extracellular signal acts indirectly, for example by up-regulating the expression of a competing factor which can sequester one or both fusion proteins. Changes in β-lactamase activity may be correlated with the expression levels of known inhibitors of differentiation such as Id proteins, measured by Northern blot in parallel samples. A comparison of the kinetics of changes in β-lactamase activity obtained with each pair of test proteins in parallel experiments will indicate whether specific MRFs (muscle regulatory factors, Yun et al. (1996) *Curr. Opin. Cell Biol.* 8:877-879; and Cossu et al. (1996) *Trends Genet.*, 12:218-223) or inhibitors differ in their ability to respond to extracellular signals. When a growth factor or substrate capable of influencing heterodimer formation (or nuclear translocation) is identified, the experiments are repeated in other, non-myogenic cell types. The analysis of the effect of a specific growth factor in different cell types would indicate whether the intracellular components of the corresponding signal transduction pathway are tissue-specific.

These studies in tissue culture cells would permit the relative affinity and compartmentalization of specific protein partners under conditions of growth and differentiation, and subsequently in response to known signal transducers, to be evaluated. The interactions of these factors may be tested in a relevant physiological background in competition with the prevalent endogenous components present in the cell at the time. Most analyses of the interactions of myogenic factors performed thus far have been carried out in vitro, in purified systems, or in yeast (Benezra et al., *Cell*, 61:1213-1230 (1990); Lassar et al., *Cell*, 66:305-315 (1991); Hu et al., *Mol. Cell. Biol.*, 12:1031-1042 (1992); Chen et al., *Cell*, 86:731-741 (1996); and Spicer et al., *Science*, 272:1476-1480 (1996). The relatively low sensitivity of the biochemical methods used to directly detect interactions in mammalian cells, such as immunoprecipitation or activation of a reporter gene construct, required high levels of protein and overexpression of the construct, usually obtained by transient transfection, levels that could potentially force an interaction due to increased concentration. The methods disclosed herein permit protein-protein interactions that are functionally relevant at different points in the myogenic differentiation pathway to be studied. Clearly, the extracellular and intracellular milieu determines the stoichiometry and abundance of the these proteins at different times. As a result, competition of different proteins for the same dimerization partners, cofactors, and kinases or phosphatases in signal transduction pathways could have significant effects on which complexes actually form in intact cells. To assess the nature of such endogenous interactions, low expression levels are needed in order not to alter the levels inherent to the cell and characteristic of the "competitive" environment at a given time.

Advantageously, high-level expression of the introduced proteins is not required in the systems described herein in order to assess the protein-protein interactions of interest. Indeed, by contrast with transient transfection assays or even most retroviral vectors with strong promoters and high translation efficiencies, the systems disclosed herein provide levels that should not perturb the natural endogenous physiological levels of the proposed test proteins in the cell.

Example 10

Analysis of Inhibitory and Myogenic HLH Proteins in Mice

The heterodimerization of inhibitory and myogenic HLH proteins in mice may be mapped. Mtwist and I-mf have been shown to inhibit myogenesis in mammalian tissue culture systems. In addition, they have been proposed to act via direct physical association with myogenic HLH proteins (Hebrok et al., *Dev. Biol.*, 165:537-544 (1994); Rohwedel et al., *Exp. Cell Res.*, 220:92-100 (1995); Chen et al., *Cell*, 86:731-741 (1996); Spicer et al., *Science*, 272:1476-1480 (1996)). During embryogenesis, Mtwist is expressed throughout the epithelial somite and is later excluded from the myotome (Fuchtbauer, *Dev. Dyn.*, 204:316-322 (1995); and Stoetzel et al., *Mech. Dev.* 51:251-263 (1995)). Although I-mf expression has not been analyzed at early stages of somatogenesis, at 11.5 days post-coitum I-mf is highly expressed in the sclerotome but is excluded from the myotome (Chen et al., *Cell*, 86:731-741 (1996)). Thus, based on their expression domains in the embryo, these factors are thought to be critical for spatial and temporal restriction of the myogenic program in early development.

Further support for this hypothesis derives from analyses of myf5/lacZ embryos in which the myf5 coding region has been targeted and replaced by lacZ. Using β-gal as a marker of the myf5 expression pattern, cells expressing myf5 are detected in the presomatic mesoderm, where Mtwist is also expressed (Fuchtbauer, *Dev. Dyn.*, 204:316-322 (1995); and Stoetzel et al., *Mech. Dev.* 51:251-263 (1995)), long before the onset of myogenesis (Cossu et al., *Trends Genet.*, 12:218-223 (1996)). Later in development, myf5 and myoD are co-expressed together with Mtwist in the somite before the formation of a distinct myotome. Ott, et al., *Development*, 111: 1097-1107 (1991); Fuchtbauer, *Dev. Dyn.*, 204:316-322 (1995); Stoetzel et al., *Mech. Dev.* 51:251-263 (1995); and Cossu et al., *Trends Genet.*, 12:218-223 (1996)). These cells do not express other detectable myogenic markers (Ott, et al., 1991). Thus, the reporter systems disclosed herein may be used to determine if the myf5 and MyoD proteins in these cells are maintained in an inactive state by interaction with Mtwist and/or I-mf in heterodimers. At subsequent stages of development, Mtwist and I-mf are expressed in most of the non-myogenic mesoderm, where the expression of myogenic factors is excluded. Smith et al., *J. Cell Biol.*, 127:95-105 (1994); Fuchtbauer, *Dev. Dyn.*, 204:316-322 (1995); Stoetzel et al., *Mech. Dev.* 51:251-263 (1995); and Chen et al., *Cell*, 86:731-741 (1996). Possibly Mtwist and I-mf are involved in the creation of a sharp border between the myotome and the adjacent tissues at this stage.

The reporter systems disclosed herein permit detailed studies of the interactions between myogenic inhibitors and activators in vivo during embryonic development which can provide novel insights into the complex process of patterning during somatogenesis. Such studies are not limited to mice and can easily be performed in *C. elegans, Drosophila, Xenopus*, zebrafish and other experimental organisms. To date, a methodology that allows visualization of protein complexes in situ in the embryo has not been available. As a result, no definitive evidence is available as to when and where during embryonic development interactions of such HLH heterodimers might occur.

Example 11

Detection of HLH Heterodimers in Mouse Embryos

The β-lactamase complementation assay is well-suited for the detection of protein-protein interactions in vivo. Myf5-Δα, MyoD-Δα and Mtwist-Δω fusion proteins may be constructed. Mediation of β-lactamase complementation with these fusion proteins may be tested in the course of performing the experiments described above. Using well-established transgenic technology (Thomas and Capecchi, *Nature*, 324: 34-38 (1986); and Capecchi, *Science*, 244: 1288-1292 (1989)), mouse lines may be generated in which one of the myf5, MyoD or Mtwist alleles has been replaced with the corresponding fusion protein. Thus myf5-Δα, MyoD-Δα and Mtwist-Δω fusion proteins will be expressed under the control of their endogenous promoters. The expression of the test protein can be verified in these mice. The Mtwist-Δω transgenic mouse may then be crossed with the myf5-Δα, and the MyoD-Δα transgenic mouse lines, and in each case the offspring may be analyzed in order to identify those carrying both of the fusion proteins. β-lactamase activity should only develop in those cells of the embryo in which Mtwist-Δω physically associates with the myf5-Δα or the MyoD-Δα fusion proteins. This analysis allows mapping when and where during embryonic development Mtwist is actually interacting with myf5 and MyoD to repress the myogenic phenotype.

Example 12

Targeting Strategy and Engineering of Necessary Constructs

The myf5-Δα fusion protein coding sequence may be inserted into the myf5 locus so that it will be expressed under the control of the endogenous myf5 regulatory elements. An insertion of wild type β-gal in the myf5 locus resulting in a fusion with the ATG of myf5 has been shown to reproduce faithfully the expression pattern of the endogenous gene. A similar strategy may be employed using β-lactamase. The targeting construct is based on the published myf5/lacZ targeting construct (Tajbakhsh and Buckingham, *Proc. Natl. Acad. Sci. USA*, 21:747-751 (1994); Tajbakhsh et al., *Neuron*, 13:813-821 (1994); and Tajbakhsh et al., *Nature* 384:266-270 (1996)), but with the following differences: (1) The fusion protein contains the complete myf5 coding sequence fused to the Δα β-lactamase. (2) The fusion protein coding sequence is followed by a neomycin resistance gene flanked by FRT sites (FLP recombinase targets). This allows G418 selection of ES cells that have taken up and integrated the targeting construct. (3) A diphtheria toxin expression cassette is located 5' of the region of homology with the myf5 mouse genomic DNA. During homologous recombination, strand exchange will occur within the homology region and as a result the diphtheria toxin expression cassette will be excluded following integration (Capecchi, *Science*, 244: 1288-1292 (1989)). Clones resulting from random integration rather than homologous recombination retain diphtheria toxin expression and will be selected against during culture, because they will die. The surviving clones are characterized by PCR, and the appropriate integration of the construct in the myf5 genomic locus is confirmed by Southern blot.

Subsequently, the neomycin selection cassette is removed using a modified version of a previously described technique (Fiering et al., *Genes Dev.*, 9:2203-2213 (1995)). Briefly, a plasmid expressing a bicistronic message containing FLP recombinase, an Internal Ribosomal Entry Site (IRES) and GFP is transiently transfected into the ES cell clones. GFP positive cells are clonally sorted using the fluorescence activated cell sorter (FACS). In these cells, FLP deletes the sequences between the two FRT sites, and only the β-lactamase coding sequence remains in the ES cell genome. Aliquots of the sorted clones are tested for sensitivity to G418, and in the sensitive clones the accurate deletion of the neomycin cassette is confirmed by PCR and Southern blotting. This approach, which eliminates the selectable marker, avoids interference between the exogenous promoter driving the selectable marker and the endogenous regulatory sequences as described (Olson et al., *Cell*, 85:1-4 (1996)).

Targeting constructs for MyoD and Mtwist have also been described (Rudnicki et al., *Cell*, 71:383-390 (1992); Chen and Behringer, *Genes Devel.*, 9:686-699 (1995)) and the relevant constructs may be produced for each. Based on these available reagents, and following the scheme proposed above for the myf5-Δα strategy, vectors to target (Chen and Behringer, *Genes Devel.*, 9:686-699 (1995)) MyoD-Δα and Mtwist-Δω fusions into the endogenous MyoD and Mtwist loci of ES cells may be constructed. In each case, an ES cell line syngeneic to the available genomic DNA homology regions in the targeting construct are used, as strain differences are known to reduce the frequency of homologous recombination. The same FLP-mediated excision methodology used for the myf5 "knock in" described above is applied to the deletion of the neomycin resistance markers from the targeted MyoD and Mtwist loci. This "in-out" strategy ensures that the fusion protein coding regions are under the control of the endogenous regulatory elements and associated with minimal extraneous flanking DNA sequences.

Example 13

Monitoring EGF Receptor Dimerization in Mammalian Cells

The regulation of the epidermal growth factor (EGF) receptor signaling pathway and other receptor signaling pathways which act through receptor dimerization can be studied using the methods of the invention for monitoring protein-protein interactions at the membrane of live mammalian cells. Chimeric proteins containing the extracellular and transmembrane domains of the EGF receptor, fused to weakly complementing β-lactamase fragments can be expressed in myoblasts. Treatment of the cells with EGF will result in chimeric receptor dimerization as assessed by a rapid increase in β-lactamase enzymatic activity. The use of such a system might be used to study aspects of receptor signaling such as feedback mechanisms in which tyrosine kinase activity of the dimeric receptor inhibits further dimerization of the receptor.

Construction of chimeric receptors The weakly complementing Δα and Δω deletion mutants of β-lactamase can each be linked to a polypeptide sequence containing the extracellular and transmembrane domains of the human EGF receptor to form chimeric receptor molecules. The chimeric receptors lack the cytoplasmic domain, and attendant tyrosine kinase activity, of the native receptor. Constructs containing the appropriate β-lactamase-EGF receptor fusions can be made using standard molecular biological cloning methods. see Sambrook et al. (Molecular Cloning: A Laboratory Manual, 2nd Ed., Cold Spring Harbor Laboratory Press, New York, N.Y. (1989)).

DNAs encoding the chimeric receptors can be inserted into retroviral vectors also encoding a selectable marker. For the construct containing the EGF receptor-Δα fusion, the selectable marker can be the neo gene, encoding G418 resistance; while the EGF receptor-Δω fusion can use hygromycin resistance. Plasmids can be transfected into φNX cells using Lipofectamine (Life Technologies), and virus-containing supernatant can be harvested 48-72 hours later. C2F3 mouse myoblasts (Rastinejad et al. (1993) *Cell* 72:903-917) maintained in DME with 20% fetal bovine serum (FBS) in 10% $CO_2$, can be infected by overnight incubation in the viral supernatant. Cells containing both constructs can be selected in 1 mg/ml G418 plus 1 mg/ml hygromycin, and maintained in 400 μg/ml of each antibiotic.

EGF treatment and FACS analysis. Cells can be treated with mouse salivary gland EGF (Sigma) at 100 ng/ml and in some experiments they can be treated with tyrphostin AG1478 (Calbiochem) at 100 nM. Following all treatments, cells can be rinsed with phosphate buffered saline (PBS), trypsinized, and resuspended in PBS+5% FBS. CCF2/AM can be loaded into the cells. Cells will be kept on ice until analysis on the cell sorter, which can be conducted 1 to 2 hours after trypsinization.

The chimeric receptor can be detected by immunofluorescence using a monoclonal mouse anti-human EGF receptor antibody diluted 1:100 (clone EGFR1, Dako) and either phycoerythrin-labeled horse anti-mouse IgG (Vector) or fluorescein-labeled goat anti-mouse IgG (Cappel) diluted 1:100. Cells can be trypsinized and stained in PBS+5% FBS. For each sample, FACS analysis data can be collected for 5000 cells. Cells can be cloned on a Becton-Dickinson FACS Vantage and analyzed on a Becton-Dickinson FACScan at the Stanford Shared FACS Facility. Data analysis can be facilitated by FlowJo software (Tree Star, Inc.). Mean fluorescence data can be adjusted for autofluorescence by subtracting the mean fluorescence of untransduced cells loaded with CCF2/AM substrate.

Receptor dimerization assay. The two chimeric DNAs can each be cloned into retroviral vectors encoding selectable markers and transduced into the C2F3 mouse myoblast cell line. After selection with G418 and hygromycin, β-lactamase enzyme activity can be monitored using the fluorescence activated cell sorter (FACS) to measure the product of a fluorogenic substrate. In the absence of EGF, the population of transduced cells would be expected to consist of a mixture of cells with low and high levels of β-lactamase activity, which would not be unexpected given that the EGF receptor is capable of dimerizing in the absence of EGF. Gadella et al. (1995) *J. Cell Biol.* 129:1543-1558. Following stimulation of the population of cells with EGF many of the cells would be exhibited to show increased β-lactamase activity. Using FACS analysis with an antibody specific to the human EGF receptor, clones can be isolated and screened for low background levels of β-lactamase activity in the absence of EGF, and increased levels of β-lactamase activity in the presence of EGF. The effect on EGF receptor dimerization of other EGF-like growth factors that bind and activate the EGF receptor, such as TGF-α, heparin-binding EGF-like growth factor, and betacellulin; and EGF-like factors, such as heregulin α, that act through related receptors other than the EGF receptor can also be studied. Beerli et al. (1996) *J. Biol. Chem.* 271:6071-6076. Dimerization can be expressed as the mean fluorescence or β-lactamase activity of the cells.

Time-course of EGF Receptor dimerization. In order to follow the fate of receptor dimers over time, cells from the an isolated clone can be cultured in media containing EGF for 0 to 24 hours and then analyzed by FACS. The time course of dimerization can then be studied. Concurrently, a measurement of the levels of the chimeric receptor on the cell surface by immunofluorescence using FACS can be used to determine whether the amount of chimeric receptor on the cell surface remains essentially constant over the period that dimerization occurs.

Feedback regulation of EGF Receptor dimerization. This invention can be used to monitor feedback regulation of the EGF receptor. The complementation of β-lactamase activity can be used as a measure of dimerization. The effect of continued EGF treatment of the cells could be measured. By measuring the effect of continued application of EGF on EGF-mediated dimerization of the chimeric receptor, one can determine if feedback regulation of EGF receptor signaling is occurring. For instance, resistance to dimerization of the EGF chimeric receptor despite continued application of EGF might indicate that signaling through the endogenous wild-type EGF receptors in the cells inhibits dimerization of the chimeric receptor. This possibility could then be further tested by using an inhibitor of the EGF receptor such as AG1478, a highly specific inhibitor of the EGF receptor tyrosine kinase. Levitzki et al. (1995) *Science* 267:1782-1788.

Accordingly, cells expressing chimeric receptor can be treated with EGF overnight, and then retreated with EGF or tyrphostin and the extent of dimerization can be determined by measuring β-lactamase activity.

Thus, the methods and compositions of the invention can be used to monitor EGF receptor dimerization in live cells. Such experiments would be expected to yield information on regulation of receptor dimerization by phosphorylation. Such a system would also afford a screening method for the identification of agents that might affect receptor dimerization.

The kinetics of complementation reflect the kinetics of association of the binding partners. The time course of dimerization of the EGF receptor chimera can be compared to the time course of the interaction of FRAP and FKBP12. β-lactamase complementation can be used to detect the rapamycin-mediated interaction between FRAP and FKBP12 as described above. Such experiments would show whether the rate of dimerization was due to the kinetics of interaction of the non-β-lactamase portions of the chimeric proteins. Such experiments would also show that β-lactamase complementation can be used to monitor the regulation of dimerization by other proteins.

Comparison to previous methods. Receptor dimerization has typically been studied by in vitro methods such as chemical cross-linking and immunopurification, followed by gel electrophoresis. Yarden et al. (1987) Biochemistry 26:1443-1451. Recently, EGF receptor dimerization has also been analyzed by fluorescence resonance energy transfer (FRET). Gadella et al. (1995) supra. Fluorescein and rhodamine labeled EGF was added to cells, and dimerization of the receptor was measured microscopically. Low temperature incubations and fixation of the cells was required to prevent internalization of the receptor before analysis, a problem that can be avoided by using a non-internalizing mutant receptor. FRET can also be used to study interactions of fluorescently-labeled molecules within the cell or cell membrane; however, labeling and introduction of these molecules at sufficiently high concentration can be cumbersome. It has recently been shown that green fluorescent protein can be modified and used for FRET analysis on genetically expressed proteins. Miyawaki et al. (1997) *Nature* 388:882-887. However, the GFP signal, however, cannot be enzymatically amplified as is the case with β-galactosidase (Blakely et al., Nat. Biotechnol. 18:218-222 (2000)) or β-lactamase.

Thus, β-lactamase complementation provides a rapid method for monitoring receptor dimerization in live cells. This method can be used for high throughput screening for pharmacological agents that can bind to a number of receptors and act as either agonists or antagonists. Binding data alone cannot indicate whether or not an agent can elicit a response; identifying a response, by analysis of downstream effects such as phosphorylation, involves destruction of the cells followed by in vitro analysis. β-lactamase complementation will also enable a screen for novel dimerization partners in a mammalian "two-hybrid" assay that, in the case of membrane receptors, can offer new insight into the regulation of signal transduction pathways.

Although the foregoing invention has been described in some detail by way of illustration and example for purposes of clarity of understanding, it will be apparent to those skilled in the art that certain changes and modifications may be practiced. Therefore the foregoing descriptions and examples should not be construed as limiting the scope of the invention.

All publications and patent applications cited in this specification are herein incorporated by reference as if each individual publication or patent application were specifically and individually indicated to be incorporated by reference.

What is claimed is:

1. A method for determining the occurrence of binding between a first and a second putative binding moiety in a eukaryotic cell, the method comprising:
   a) providing a beta-lactamase enzyme complementation reporter system comprising:
      a first component comprising a first beta-lactamase enzyme fragment coupled to the first putative binding moiety wherein the first beta-lactamase enzyme fragment is about 19 kDa in size; and
      a second component comprising a second beta-lactamase enzyme fragment coupled to the second putative binding moiety wherein the second beta-lactamase enzyme fragment is about 10 kDa in size;
      wherein the first beta-lactamase enzyme fragment and the second beta-lactamase fragment are complementing beta-lactamase enzyme fragments, wherein beta-lactamase enzyme complementation occurs when the first putative binding moiety binds to the second putative binding moiety;
   b) combining the first component and the second component in a eukaryotic cell; and
   c) detecting beta-lactamase enzyme complementation in the eukaryotic cell, wherein detection of beta-lactamase enzyme complementation and resultant beta-lactamase enzymatic activity indicates the occurrence of binding between the first and second binding moieties in the eukaryotic cell.

2. The method of claim 1 wherein the binding affinity of the first and second putative binding moieties for each other is greater than the binding affinity of the first and second beta-lactamase enzyme fragments for each other.

3. The method of claim 2 wherein the first and second putative binding moieties are proteins.

4. The method of claim 3 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translation regulatory proteins, proteins that affect cell interactions, cell adhesion molecules, proteins which are members of ligand-receptor pairs, proteins that participate in the folding of other proteins, and proteins involved in targeting to intracellular compartments.

5. The method of claim 1, wherein the detecting step comprises:
   incubating the first and second component with a substrate, wherein the substrate is converted to a detectable product by beta-lactamase enzyme; and
   detecting a detectable signal produced by the detectible product.

6. The method of claim 5, wherein the detectable signal is directly detectable with a substrate for beta-lactamase.

7. The method of claim 5, wherein the detectable signal is amplifiable.

8. The method of claim 5, wherein the detectable signal is generated in situ in the eukaryotic cell.

9. The method of claim 1, wherein each of said first and second components comprises a fusion protein.

10. The method of claim 9 wherein step (b) comprises transforming the eukaryotic cell with one or more nucleic acids encoding the fusion proteins.

11. The method of claim 10 wherein the one or more nucleic acids encoding the fusion proteins further comprise sequences regulating expression of the putative binding protein.

12. The method of claim 10 wherein the fusion proteins are encoded by a viral vector.

13. The method of claim 9 wherein the fusion protein further comprises a protein sequence between said beta-lactamase enzyme fragment and said putative binding moiety.

14. The method of claim 1, wherein the method further comprises:
   (d) detecting the effect of a third moiety on the binding of the first and second binding moieties by combining said reporter system with said third moiety following step (b) and prior to step (c).

15. The method of claim 8 wherein the intracellular localization of the detectible signal is determined.

16. The method of claim 1, wherein:
   step (b) further comprises incubating the first and second components in the presence and absence of a substance; and
   step (c) further comprises detecting the beta-lactamase enzyme complementation in the presence and absence of the substance;
   wherein a difference in the beta-lactamase enzyme complementation is an indication that-the substance affects binding of the first and second binding moieties.

17. The method of claim 16 wherein the substance is a peptide, drug or synthetic analog.

18. The method of claim 16 wherein the substance is a putative inhibitor of binding between the first and second binding moieties, and wherein the detected beta-lactamase enzyme complementation is lower in the presence of the substance than in the absence of the substance.

19. The method of claim 16 wherein the substance is a putative promoter of binding between the first and second binding moieties, and wherein the detected beta-lactamase enzyme complementation is higher in the presence of the substance than in the absence of the substance.

20. The method of claim 16 wherein the first and second binding moieties are proteins; the first and second components of step (a) each comprise a fusion protein; step (b) further comprises expressing nucleic acid sequences encoding the first and second components within a cell suspected to contain the substance, wherein the substance inhibits or promotes binding of the binding moieties; and step (c) further comprises detecting the beta-lactamase enzyme complementation in the cell or a lysate thereof, wherein the detected complementation correlates with a presence or absence in the cell of the substance.

21. The method of claim 16 wherein the substance is selected from the group consisting of a protein, lipid, carbohydrate, nucleic acid, and a small molecule pharmaceutical.

22. A method of screening for binding of a first binding moiety with members of a plurality of different second putative binding moieties in a eukaryotic cell, the method comprising:
   a) providing a plurality of beta-lactamase enzyme complementation reporter systems each comprising:
      a first component comprising a first beta-lactamase enzyme fragment coupled to the first binding moiety wherein the first beta-lactamase enzyme fragment is about 19 kDa in size; and
      a second component comprising a second beta-lactamase enzyme fragment coupled to one of said plurality of different second putative binding moieties wherein the second beta-lactamase enzyme fragment is about 10 kDa in size;
      wherein the first beta-lactamase enzyme fragment and the second beta-lactamase enzyme fragment are complementing beta-lactamase enzyme fragments, wherein beta-lactamase enzyme complementation occurs when the first binding moiety and one of said different second putative binding moieties bind to one another;
   b) combining the first component and the second component of each of the plurality of beta-lactamase enzyme complementation reporter systems in a corresponding plurality eukaryotic cells, wherein each of the corresponding plurality of eukaryotic cells includes the first component and a corresponding different one of the second components, wherein the first component is in each of the corresponding plurality of eukaryotic cells; and
   c) detecting beta-lactamase enzyme complementation in each of the corresponding plurality of eukaryotic cells, wherein detection of beta-lactamase enzyme complementation and resultant beta-lactamase enzymatic activity in one of the corresponding plurality of eukaryotic cells indicates binding of the first binding moiety with the second putative binding moiety of the corresponding second component in the eukaryotic cell.

23. The method of claim 22, wherein the first and second components each comprise a fusion protein including the binding moiety and the beta-lactamase enzyme fragment.

24. The method of claim 23, wherein, in step (b), the components are expressed from a nucleic acid sequence introduced into the eukaryotic cell.

25. The method of claim 24, wherein the plurality of second putative binding moieties are encoded by members of a cDNA library.

26. The method of claim 22, wherein the eukaryotic cell is a mammalian cell.

27. The method of claim 26, wherein the cell is a human cell.

28. The method of claim 22, wherein, in step (c), beta-lactamase enzyme complementation is quantitated.

29. The method of claim 22, wherein the detecting step comprises:
   incubating the first and second component with a substrate, wherein the substrate is converted to a detectable product by beta-lactamase enzyme; and
   detecting a detectable signal produced by the detectable product.

30. The method of claim 29, wherein the detectable signal is directly detectable.

31. The method of claim 29, wherein the detectable signal is amplifiable.

32. The method of claim 29, wherein the detectable signal is generated in situ in the eukaryotic cell.

33. The method of claim 22, wherein eukaryotic cells in which binding between the first binding moiety and one of the plurality of different putative second binding moieties has occurred are separated from eukaryotic cells in which said binding has not occurred.

34. The method of claim 33, wherein the separation is by fluorescence-activated cell sorting.

35. The method of claim 22, wherein the first binding moiety is selected from the group consisting of cell surface receptors, transcriptional regulatory proteins, translation regulatory proteins, replication proteins, splicing proteins, signal transduction proteins, cell-cell adhesion molecules, cell-substrate adhesion molecules, cell-cycle proteins, oncogene products, tumor suppressor proteins, membrane receptors, proteins regulating apoptosis, developmental regulatory proteins, proteins that affect cell interactions, proteins that participate in the folding of other proteins, proteins involved in targeting to intracellular compartments, viral proteins, and cytoskeletal proteins.

36. The method of claim 3 wherein the first beta-lactamase enzyme fragment contains a tripeptide inserted between a carboxy terminus of the fragment and a linker to the first putative binding moiety.

37. The method of claim 3 wherein the beta lactamase is TEM-1 beta-lactamase.

* * * * *

SEQUENCE LISTING

```
<160> NUMBER OF SEQ ID NOS: 6

<210> SEQ ID NO 1
<211> LENGTH: 51
<212> TYPE: DNA
<213> ORGANISM: E.coli
```

```
<400> SEQUENCE: 1
tcgagggtgg aggcggttca ggcggaggtg gcagcggcgg tggcggatcg g          51

<210> SEQ ID NO 2
<211> LENGTH: 22
<212> TYPE: DNA
<213> ORGANISM: E.coli

<400> SEQUENCE: 2
ctcgagcacc cagaaacgct gg                                          22

<210> SEQ ID NO 3
<211> LENGTH: 22
<212> TYPE: DNA
<213> ORGANISM: E.coli

<400> SEQUENCE: 3
gcttttaccc gcccttcagc tg                                          22

<210> SEQ ID NO 4
<211> LENGTH: 24
<212> TYPE: DNA
<213> ORGANISM: E.coli

<400> SEQUENCE: 4
ctcgagggag tgcaggtgga aacc                                        24

<210> SEQ ID NO 5
<211> LENGTH: 22
<212> TYPE: DNA
<213> ORGANISM: E.coli

<400> SEQUENCE: 5
cgaagatttt gaccttcagc tc                                          22

<210> SEQ ID NO 6
<211> LENGTH: 15
<212> TYPE: PRT
<213> ORGANISM: Artificial
<220> FEATURE:
<223> OTHER INFORMATION: synthetic

<400> SEQUENCE: 6

Gly Gly Gly Gly Ser Gly Gly Gly Gly Ser Gly Gly Gly Gly Ser
1               5                   10                  15
```